US010172795B2

(12) United States Patent
Gao et al.

(10) Patent No.: US 10,172,795 B2
(45) Date of Patent: Jan. 8, 2019

(54) FORMULATIONS AND CARRIER SYSTEMS INCLUDING COMPOUND INTERACTIVE DOMAINS

(71) Applicant: University of Pittsburgh—Of The Commonwealth System of Higher Education, Pittsburgh, PA (US)

(72) Inventors: Xiang Gao, Pittsburgh, PA (US); Song Li, Wexford, PA (US); Peter Wipf, Pittsburgh, PA (US); Michael Wayne Epperly, Pittsburgh, PA (US); Joel S. Greenberger, Sewickley, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/651,840

(22) PCT Filed: Dec. 12, 2013

(86) PCT No.: PCT/US2013/074684

§ 371 (c)(1),
(2) Date: Jun. 12, 2015

(87) PCT Pub. No.: WO2014/093631

PCT Pub. Date: Jun. 19, 2014

(65) Prior Publication Data

US 2015/0306034 A1 Oct. 29, 2015
US 2016/0128938 A9 May 12, 2016

Related U.S. Application Data

(60) Provisional application No. 61/736,100, filed on Dec. 12, 2012.

(51) Int. Cl.

| | |
|---|---|
| ***A61K 31/45*** | (2006.01) |
| ***A61K 9/107*** | (2006.01) |
| ***A61K 9/127*** | (2006.01) |
| ***A61K 31/337*** | (2006.01) |
| ***A61K 31/704*** | (2006.01) |

(52) U.S. Cl.

CPC .......... *A61K 9/1075* (2013.01); *A61K 9/1271* (2013.01); *A61K 31/337* (2013.01); *A61K 31/45* (2013.01); *A61K 31/704* (2013.01)

(58) Field of Classification Search

CPC ................................................... A61K 9/1075
USPC ......................................................... 424/450
See application file for complete search history.

(56) References Cited

U.S. PATENT DOCUMENTS

2011/0065807 A1 3/2011 Radovic-Moreno
2011/0117024 A1 5/2011 Sinko
2012/0309780 A1 12/2012 Kwon

FOREIGN PATENT DOCUMENTS

WO WO2007086651 * 8/2007
WO WO2014093631 A1 6/2014

OTHER PUBLICATIONS

Bhadra (J Pharm Pharmaceut Sci 8 (3):467-482, Sep. 2, 2005).*
Lukyanov (Advanced Drug Delivery Reviews 56 (2004) 1273-1289).*
Rajagopalan (in vivo 23: 717-726 (2009)).*
Tian (J. Mater. Chem., 2004, 14, 2317-2324).*
Lu. J. eL al., PEG_derivatized embelin as a nanomicellar carrier for delivery of paclitaxel to breast and prostate cancers, Biomaterials, Nov. 23, 2012 (E-pub), vol. 34, 1591-1600.
Xiao, K. et a!, A self-assembling nanoparticle for paclitaxel delivery in ovarian cencer, Biomaterials, 2009, vol. 30, 6006-6016.
Gao, X. et al., Nanoassembly of surfactants with interfacial drug-interactive motifs as tailor-designed drug carriers, Molecular Pharmaceutics, Dec. 17, 2012 (E-pub), vol. 10, 187-198.
Bhadra D. et al., Pegylated Lysine Based Copolymeric Dendritic Micelles for Solubilization Ans Delivery of Artemether, Journal of Pharmacy and Pharmaceutical Sciences, Canadian Society for Pharmaceutical Sciences, Edmonton, CA, vol. 8. No. 3, Sep. 2, 2005, pp. 467-482.
Sang Cheon Lee et al, Hydrotropic Polymeric Micelles for Enhanced Paclitaxel Solubility: In Vitro and In Vivo Characterization, Biomacromolecules, vol. 8. No. 1, Dec. 1, 2006, pp. 202-208.
Saravanakumar G et al., Hydrotropic hyaluronic acid conjugates: Synthesis, characterization and implications as a carrier of paclitaxel, International Journal of Pharmaceutics, Elsevier BV, NL, vol. 394. No. 1-2, Jul. 15, 2010, pp. 154-161.
Saravanakumar G et al., Hydrotropic oligomer-conjugated glycol chitosan as a carrier of paclitaxel: Synthesis characterization and in vivo biodistribution, Journal of Controlled Release, Elsevier, Amsterdam, NL, vol. 140, No. 3, Dec. 16, 2009, pp. 210-217.
Ian W. Hamley et al., A Thermoresponsive Hydrogel Based on Telechelic PEG End-Capped with Hydrophobic Dipeptides, Macromolecular Bioscience, vol. 11, No. 8, May 6, 2011, pp. 1068-1078.
Peng Zhang et al., Design and Evaluation of a PEGylated Lipopeptide Equipped with Drug-Interactive Motifs as an Improved Drug Carrier, The AAPS Journal, vol. 16, No. 1, Nov. 27, 2013, pp. 114-124.

(Continued)

*Primary Examiner* — Devang K Thakor

(74) *Attorney, Agent, or Firm* — Bartony & Associates, LLC

(57) ABSTRACT

A method of creating a formulation for a compound includes determining a compound interactive agent comprising at least one group that interacts with the compound, creating a carrier agent by conjugating at least one compound interactive domain comprising the at least one group that interacts with the compound with at least one hydrophilic domain, and combining the compound and the carrier agent to create the formulation. Creating the carrier agent may further include conjugating the at least one compound interactive domain with at least one hydrophobic domain so that the at least one compound interactive domain is positioned between the at least one hydrophilic domain and the at least one hydrophobic domain.

17 Claims, 14 Drawing Sheets

(56) References Cited

OTHER PUBLICATIONS

Ischakov Rafael et al., Peptide-based hydrogel nanoparticles as effective drug delivery agents, Bioorganic & Medicinal Chemistry, Pergamon, GB, vol. 21, No. 12, Mar. 21, 2013, pp. 3517-3522.
Xiaolan Zhang et al., PEG-Farnesylthiosalicylate Conjugate as a Nanomicellar Carrier for Delivery of Paclitaxel, Bioconjugate Chemistry, vol. 24, No. 3. Mar. 20, 2013, pp. 464-472.
Jianqin Lu et al., Design and Characterization of PEG-Derivatized Vitamin E as a Nanomicellar Formulation for Delivery of Paclitaxel, Molecular Pharmaceutics, vol. 10, No. 8, Aug. 5, 2013, pp. 2888-2898.
Beg, Sarwar, Bioavailability Enhancement Strategies: Basics, Formulation Approaches and Regulatory Considerations, Current Drug Delivery, 2011, vol. 8, No. 6, pp. 1-12.
Nanjwade, Basavaraj K., Functions of Lipids for Enhancement of Oral Bioavailability of Poorly Water-Soluble Drugs, Sci Pharm. 2011; 79: 705-727.
Buse, Joshua, Properties, engineering and applications of lipid-based nanoparticle drug-delivery systems: current research and advances,Nanomedicine (2010) 5(8), 1237-1260.
Puri, Anu et al., Lipid-Based Nanoparticles as Pharmaceutical Drug Carriers: From Concepts to Clinic, Crit Rev Ther Drug Carrier Syst. 2009 ; 26(6): 523-580.
Narang, Ajit S. et al., Stable drug encapsulation in micelles and microemulsions, International Journal of Pharmaceutics 345 (2007) 9-25.
Jiang, Jianfei et al., A Mitochondria-Targered Nitroxide/Hemigramicisin S Conjugate Protects Mouse Embryonic Cells Against Gamma Irradiation, Int J Radiat Oncol Biol Phys. Mar. 1, 2008; 70(3): 816-825.
Jiang, Jianfei et al., Structural Requirements for Optimized Delivery, Inhibition of Oxidative Stress, and Antiapoptotic Activity of Targeted Nitroxides, The Journal of Pharmacology and Experimental Therapeutics, vol. 320, No. 3, 1050-1060.
Rajagopalan, Malolan S., et al, The Mitochondria-targeted Nitroxide JP4-039 Augments Potentially Lethal Irradiation Damage Repair, in vivo 23: 717-726 (2009).
Epperly, Michael W., et al.,Intraesophageal Administration of GS-Nitroxide (JP4-039) Protects Against Ionizing Irradiation-induced Esophagitis, in vivo 24: 811-820 (2010).
Epperly, M., et al., Topical Application of GS-Nitroxide JP4-039 Emulsion Mitigates Ionizing Irradiation Induced Skin Burns, Int. J. Radiation Oncology Biol. Physics. 78(2010)S634-S635.
Goff, Julie P., et al., Radiobiologic Effects of GS-Nitroxide (JP4-039) on the Hematopoietic Syndrome, in vivo 25: 315-324 (2011).
Frantz, Celine-Marie, et al., Large-Scale Asymmetric Synthesis of the Bioprotective Agent JP4-039 and Analogs, Organic Letters (2011), Vo. 13, No. 9, 2318-2321.
Zalipsky, S., et al., Attachment of Drugs to polyethylene Glycols, Eur. Polvm. J. vol. 19, No. 12, pp. 1177 1183, 1983.
Patist, A. et al., On the Measurement of Critical Micelle Concentrations of Pure and Technical-Grade Nonionic Surfactants, Journal of Surfactants and Detergents, vol. 3, No. 1 (Jan. 2000), 53-58.
Kenworthy, A. K. et al., Range and Magnitude of the Steric Pressure Between Bilayers Containing Phospholipids with Covalently Attached Poly(ethylene glycol), Biophysical Journal vol. 68 May 1995 1921-1936.
Zhu, Peizhi et al., Fluorescence Quenching by TEMPO: A Sub-30 A° Single-Molecule Ruler, Biophys. J. 89(2005) L37-L39.
Lee, Jaehwi, et al., Hydrotropic Solubilization of Paclitaxel: Analysis of Chemical Structures for Hydrotropic Property, Pharmaceutical Research, vol. 20, No. 7, Jul. 2003, 1022-1030.
Kim, Ji Young, et al., Hydrotropic polymer micelles as versatile vehicles for delivery of poorly water-soluble drugs, Journal of Controlled Release 152 (2011) 13-20.
Dabholkar, Rupa D., et al., Polyethylene glycol-phosphatidylethanolamine conjugate (PEG-PE)-based mixed micelles: Some properties, loading with paclitaxel, and modulation of P-glycoprotein-mediated efflux, International Journal of Pharmaceutics 315 (2006) 148-157.
Luo, Juntao et al., Well-Defined, Size-Tunable, Multifunctional Micelles for Efficient Paclitaxel Delivery for Cancer Treatment, Bioconjugate Chem. 2010, 21, 1216-1224.
Yen, Chiao-Ting, et al., Design and synthesis of new N-(fluorenyl-9-methoxycarbonyl) (Fmoc)-dipeptides as anti-inflammatory agents, European Journal of Medicinal Chemistry 44 (2009) 1933-1940.
Zhang, Yan, et al., Supramolecular Hydrogels Respond to Ligand-Receptor Interaction, J. Am. Chem. Soc. 2003, 125, 13680-13681.
Jayawarna, Vineetha et al., Nanostructured Hydrogels for Three-Dimensional Cell Culture Through Self-Assembly of Fluorenylmethoxycarbonyl-Dipeptides, Adv. Mater. 2006, 18, 611-614.
Mahler, Assaf et al., Rigid, Self-Assembled Hydrogel Composed of a Modified Aromatic Dipeptide, Adv. Mater. 2006, 18, 1365-1370.
Huang, Yixian, et al., PEG-Derivatized Embelin as a Dual Functional Carrier for the Delivery of Paclitaxel Bioconjugate Chem. 2012, 23, 1443-1451.
Dong, He et al., Long-Circulationg 15nm Micelles Based on Amphiphilic 3-Helix Peptide-PEG Conjugates, ACSNANO, vol. 6, No. 6, 5320-5329.
Lukyanov, Anatoly N., et al. Micelles from Lipid Derivatives of Water-Soluble Polymers as Delivery Systems for Poorly Soluble Drugs, Advanced Drug Delivery Reviews, vol. 56, 1273-1289.

* cited by examiner

R1, R2 =

Ace

Benzyl t-Boc

Cbz

Fmoc

Isb

1

2

3

4

5

6

7

8

Fmoc =

Z =

FORMULATIONS AND CARRIER SYSTEMS INCLUDING COMPOUND INTERACTIVE DOMAINS

CROSS-REFERENCE TO RELATED APPLICATION

This application is a national phase filing of PCT International Patent Application No. PCT/US2013/074684, filed Dec. 12, 2013, which claims benefit of U.S. Provisional Patent Application Ser. No. 61/736,100, filed Dec. 12, 2012, the disclosures of which are incorporated herein by reference.

GOVERNMENTAL INTEREST

This invention was made with government support under grant nos. AI068021, GM067082, HL091828 and GM085043 awarded by the National Institutes of Health. The government has certain rights in this invention.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Poor water solubility is one of the major hurdles for the advancement of drug candidates into clinical applications. Most drug companies focus on orally deliverable drugs. Not all drugs are orally bioavailable, however. Bioavailability may, for example, be defined as the fraction of an administered dose of unchanged drug that reaches, for example, the systemic circulation. Some compounds/drugs maybe degraded in the digest tract, some maybe too harmful for the epithelial lining, and in many cases, the duration of the free drug in blood once absorbed is very short. Any one or combination of these problems for a drug candidate may result in the elimination or cessation of drug development (as a general practice in the pharmaceutical industry).

Compound dispersion and/or solubilization are thus essential first steps for many pharmaceutical agents to be administered/absorbed by body, whether it is through an oral, a topical or a systemic route. Amphiphilic agents (which have a hydrophilic segment or head and a hydrophobic segment or tail) such as surfactants and various lipid-based formulations, such as micelles, emulsion, cream, liposome, solid-lipid nanoparticles are frequently used formulation systems for poorly soluble drugs. Lipidic based formulations, such as liposomes, emulsions and micelles, are attractive drug delivery systems for in vivo applications because of their excellent safety profiles. Water-soluble polymers, polymer-based hydrogels, and polymer-nanoparticles are also useful drug delivery systems for oral, topical and systemic use.

Various types of lipidic drug formulations are currently used in a clinical setting for the treatment of cancers and infectious diseases. Current approaches for determining lipidic formulations use trial and error process by selecting proper starting materials from existing off-shelf ingredients.

Even for a more sophisticated work on synthetic molecules as a carrier, formulations are still empirical and not mechanistically based.

SUMMARY

In one aspect, a method of creating a formulation for a compound includes determining a compound interactive agent comprising at least one group that interacts with the compound, creating a carrier agent by conjugating or attaching at least one compound interactive domain including the at least one group that interacts with the compound with/to at least one hydrophilic domain, and combining the compound and the carrier agent to create the formulation. In a number of embodiments, creating the carrier agent further includes conjugating or attaching the at least one compound interactive domain with/to at least one hydrophobic domain so that the at least one compound interactive domain is positioned between the at least one hydrophilic domain and the at least one hydrophobic domain.

The at least one hydrophilic domain may, for example, include at least one hydrophilic oligomer or at least one hydrophilic polymer. The term "polymer" refers generally to a molecule of high relative molecular mass, the structure of which includes repeat units derived, actually or conceptually, from molecules of low relative molecular mass (monomers). The term "oligomer" refers generally to a molecule of intermediate relative molecular mass, the structure of which includes a small plurality of units derived, actually or conceptually, from molecules of lower relative molecular mass (monomers). In general, a polymer is a compound having >1, and more typically >10 repeat units or monomer units, while an oligomer is a compound having >1 and <20, and more typically leas than ten repeat units or monomer units. In a number of embodiments, the hydrophilic oligomer or the hydrophilic polymer is a polyalkylene oxide, a polyvinylalcohol, a polyacrylic acid, a polyacrylamide, a polyoxazoline, or a polypeptide. In a number of embodiments, the polyalkylene oxide is a polyethylene glycol. The at least one hydrophilic domain may, for example, include at least one ionic group. In a number of embodiments, the at least one hydrophilic domain includes at least one carboxylic acid group, at least one amine group, at least one saccharide group, or at least one polysaccharide group.

The compound interactive domain may, for example, include at least one amino acid group or at least one peptide group. The amino acid group or the peptide group may, for example, include at least one pendant group having an affinity for the compound. In a number of embodiments, the compound interactive domain includes at least one of a fluorenylmethyloxycarbonyl group, a carbobenzyloxy group, an isobutoxycarbamate group, a naphthylacetyl group, a carbazole group, a quinolone group, an isoquinolone group, or a group which is a residue of a molecule selected from the group of the compound, a portion of the compound or the entire compound, (9H-fluoren-9-yl)methanamine, (9H-fluoren-9-yl)methanol, 9H-fluoren-9-amine, naphthalene, 1,1'-bi-2-naphthol (BINOL), camptothecin, a camptothecin analog (for example, hydroxyl camptothecin, irinotecan, topotecan and homocamptothecins), pemetrexed, docetaxel, paclitaxel, epirubicin, doxorubicin, vinblastine, vindesine, etoposide, hydroxycamptothecin, mitoxantrone, tamoxifen, tretinoin, Vitamin A (for example, retinol, retinal, retinoic acid, and provitamin A carotenoids, such as beta-carotene), Vitamin E (for example, tocopherols and tocotrienols), Vitamin K (for example, phylloquinone or menaquinones), Vitamin D (for example, secosteroids such as cholecalciferol or ergocalciferol), curcumin, imatinib, gefitinib, erlotinib, sorafenib, and bortezomib, or a derivative thereof. In a number of embodiments, the compound interactive domain includes at least one fluorenylmethyloxycarbonyl group or a derivative thereof.

The at least one group that interacts with the compound may, for example, have an affinity for the compound. The at least group that interacts with the compound may, for example, interact with the compound via π-π stacking, hydrophobic interaction or hydrogen-bonding.

The formulation may, for example, form a complex such as, for example, a micelle, an emulsion, a cream, a liposome, a spherulite, a solid-lipid nanoparticle, a hydrogel or a cubic phase lipogel.

The at least one hydrophobic domain may, for example, at least one lipid, at least one tocopherol (for example, Vitamin E), at least one hydrophobic oligomer or at least one hydrophobic polymer. In a number of embodiments, the at least one hydrophobic domain includes at least one of a polymethylacryl, a polyethylene, a polystyrene, a polyisobutane, a polyester, a polypeptide, or a derivative thereof. In a number of embodiments, the at least one hydrophobic domain includes a farnesylthiosalicylate (FTS) group. In a number of embodiments, the at least one hydrophobic domain includes at least one lipid.

The carrier system may, for example, provide a drug loading capacity of at least 10%, at least 20%, at least 30% or even at least 40%. In general, the loading capacity of the carrier system is increased via the compound interactive domain. Likewise, the stability may also be increased. For example, an amphiphilic carrier system hereof will have a greater loading capacity than an amphiphilic molecule including only the hydrophobic domain and the hydrophilic domain of the amphiphilic carrier system hereof.

In a number of embodiments, the at least one hydrophilic domain has a molecular weight of at least 1 KDa (for example, in the range of approximately 1 KDa to 10 KDa), the at least one compound interactive domain has a molecular weight in the range of approximately 300 Da to 2 KDa, and the at least one hydrophobic domain has a molecular weight of at least 2 KDa (for example, in the range of approximately 2 KDa to 20 KDa). In a number of embodiments, the at least one hydrophilic domain has a molecular weight in the range of approximately 1 KDa to 5 KDa, and the at least one hydrophobic domain has a molecular weight in the range of approximately 2 KDa to 5 KDa. The domains may, for example, include a single or multiple chains.

In a number of embodiments, the compound is a drug. A drug is a biologically active substance which has an effect on the body (for example, a medicinal or therapeutic effect, an intoxicating effect, a performance enhancing effect or another effect). In a number of embodiments, the compound is JP4-039, paclitaxel, FK506, cyclosporin A, a protoporphyrin, GW4064, rose bengal, epigallocatechin gallate, curcumin, indomethacin, tamoxifen or doxorubicin. In a number of embodiments, the compound is paclitaxel, the hydrophilic domain includes polyethylene glycol and the interactive domain includes at least one fluorenylmethyloxycarbonyl group or a derivative thereof.

In a number of embodiments, the at least one compound interactive domain of the carrier is covalently bonded to the at least one hydrophilic domain. In a number of embodiments, the at least one compound interactive domain of carrier agent is covalently bonded to the at least one hydrophilic domain and is covalently bonded to the at least one hydrophobic domain.

In another aspect, a formulation to deliver a compound to a patient includes the compound and a carrier agent including at least one hydrophilic domain conjugated with at least one compound interactive domain. The compound interactive domain includes at least one group that interacts with the compound. In a number of embodiments, the carrier agent further includes at least one hydrophobic domain conjugated with the at least one compound interactive domain so that the at least one compound interactive domain is positioned between the at least one hydrophilic domain and the at least one hydrophobic domain.

In another aspect, a method of creating a formulation to deliver a compound to a patient includes providing a carrier agent including at least one hydrophilic domain conjugated with at least one compound interactive domain, wherein the compound interactive domain includes at least one group that interacts with the compound, and combining the compound and the carrier agent. In a number of embodiments, the carrier agent further includes at least one hydrophobic domain conjugated with the at least one compound interactive domain so that the at least one compound interactive domain is positioned between the at least one hydrophilic domain and the at least one hydrophobic domain.

In another aspect, a composition of matter includes at least one hydrophilic polymer attached to at least one group selected from the group of a fluorenylmethyloxycarbonyl group, a carbobenzyloxy group, an isobutoxycarbamate group, a naphthylacetyl group, a carbazole group, a quinolone group, an isoquinolone group, and a group which is a residue of a molecule selected from the group of (9H-fluoren-9-yl)methanamine, (9H-fluoren-9-yl)methanol, 9H-fluoren-9-amine, naphthalene, 1,1'-bi-2-naphthol (BINOL), camptothecin, a camptothecin analog, pemetrexed, docetaxel, paclitaxel, epirubicin, doxorubicin, vinblastine, vindesine, etoposide, hydroxycamptothecin, irinotecan, mitoxantrone, tamoxifen, tretinoin, Vitamin A, Vitamin E, Vitamin K, Vitamin D, curcumin, imatinib, gefitinib, erlotinib, sorafenib, and bortezomib, or a derivative thereof. The hydrophilic polymer may, for example, be a polyalkylene oxide, a polyvinylalcohol, a polyacrylic acid, a polyacrylamide, a polyoxazoline, or a polypeptide. In a number of embodiments, the hydrophilic polymer is a polyalkylene oxide. The hydrophilic polymer may, for example, be a polyethylene glycol. The polyethylene glycol may, for example, have a molecular weight of at least 1 KDa. In a number of embodiments, the polyethylene glycol has a molecular weight in the range of approximately 1 KDa to 10 KDa. The at least one group may, for example, be attached to the at least one hydrophilic polymer via at least one amino acid group or at least one peptide group.

In a number of embodiments, the at least one group is selected from the group of a fluorenylmethyloxycarbonyl group, a carbobenzyloxy group, an isobutoxycarbamate group, a naphthylacetyl group, a carbazole group, a quinolone group, an isoquinolone group, or derivatives thereof. In a number of embodiments, the at least one group is selected from the group of a fluorenylmethyloxycarbonyl group, a carbobenzyloxy group, an isobutoxycarbamate group, a naphthylacetyl group, a carbazole group, or derivatives thereof. In a number of embodiments, the at least one group is selected from the group of a fluorenylmethyloxycarbonyl group, a carbobenzyloxy group, an isobutoxycarbamate group, a naphthylacetyl group, or a carbazole group. In a number of embodiments, the at least one group is a fluorenylmethyloxycarbonyl group or a derivative thereof. The composition may, for example, be polyethylene glycol-lysyl-(α-Fmoc-ε-t-Boc-lysine)$_2$.

In a number of embodiments, the composition further includes at least one hydrophobic group, wherein the at least one group is positioned between the hydrophobic group and the at least one hydrophilic polymer. The at least one hydrophobic group may, for example, include at least one of a lipid, a polymethylacryl, a polyethylene, a polystyrene, a polyisobutane, a polyester, a polypeptide, or a derivative thereof. In a number of embodiments, the at least one hydrophobic group comprises at least one of a lipid group. The at least one hydrophobic group may, for example, includes at least one of oleyl group.

In a further aspect, a carrier agent for use with a compound includes at least one hydrophilic domain conjugated with at least one compound interactive domain which includes at least one group that interacts with the compound. In a number of embodiments, the carrier agent further includes at least one hydrophobic domain conjugated with the at least one compound interactive domain so that the at least one compound interactive domain is positioned between the at least one hydrophilic domain and the at least one hydrophobic domain.

In still a further aspect, a method of treating a patient with a compound includes delivering to the patient a formulation including the compound and a carrier agent including at least one compound interactive domain including at least one group that interacts with the compound. The at least one compound interactive group is conjugated with at least one hydrophilic domain. In a number of embodiments, the carrier agent further includes at least one hydrophobic domain conjugated with the at least one compound interactive domain so that the at least one compound interactive domain is positioned between the at least one hydrophilic domain and the at least one hydrophobic domain. The formulations may be formed via the methods described above.

The present systems, methods and compositions, along with the attributes and attendant advantages thereof, will best be appreciated and understood in view of the following detailed description taken in conjunction with the accompanying drawings.

DESCRIPTION

Figure 1:
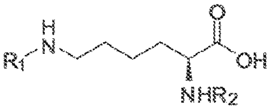
FIG. 1 illustrates structures of various amino acid derivatives studied in solubility studies of JP4-039 (a hydrophobic, peptide-TEMPO-(2,2,6,6-Tetramethylpiperidinyloxyl-) based stable nitroxide radical antioxidant).
Figure 1:
Figure 1:
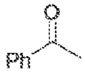
Figure 1:
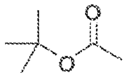
Figure 1:
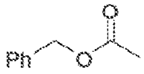
Figure 1:
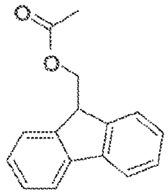
Figure 1:
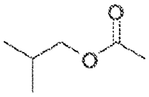

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "an interactive segment" includes a plurality of such interactive segments and equivalents thereof known to those skilled in the art, and so forth, and reference to "the interactive segment" is a reference to one or more such interactive segments and equivalents thereof known to those skilled in the art, and so forth. Recitation of ranges of values herein are merely intended to serve as a shorthand method of referring individually to each separate value falling within the range. Unless otherwise indicated herein, and each separate value as well as intermediate ranges are incorporated into the specification as if it were individually recited herein. All methods described herein can be performed in any suitable order unless otherwise indicated herein or otherwise clearly contraindicated by the text.

Existing lipid-based formulations are more applicable to either hydrophilic (for example, liposome formulations) or hydrophobic drugs (for example, liposome, micelle and emulsion formulations). However, such formulations are typically not well suited for many drugs that are only moderately hydrophobic or moderately hydrophilic. Inadequate mixing of less hydrophobic agents with highly lipophilic aliphatic chains in surfactants and in the oil core of emulsions may lead to low drug loading capacity and formulation instability. Drugs that are initially mixed with an oil core tend to slowly move to the interface of emulsion particles and eventually are disassociated from the particles. Drugs with moderate hydrophobicity or hydrophilicity also have leakage problems from liposome formulations.

Most, if not all, amphiphilic or surfactant molecules that are available on the market and used for formulation purposes have limited or very simple interfacial structure domains (if present at all). In most cases, a hydrophobic group is covalently bonded to a hydrophilic group without any interfacial or intermediate domain. Examples of amphiphilic or surfactant molecules include Triton-X100, Tweens, PEG-alkyl ether or ester, PEG-phospholipid conjugates, SDS, oleic acid or other fatty acid, mono-, di-, or triglycerides, bile acid, phospholipids, cholesterol derivatives, and tocopherol (Vitamin E) derivatives. In general the interfacial region (that is, the region between the hydrophilic head and the hydrophobic tail) of amphiphilic surfactants is underappreciated in the drug formulation process or practice. However, the interfacial region should be viewed with much more importance according to the thermodynamic principles for drug formulation. In that regard, and without limitation to any mechanism, a poorly water-soluble drug with only moderate hydrophobicity will have a stability issue for lipid-based system because the drug is too hydrophilic for the oil core, while too hydrophobic for the aqueous phase. Over time, drug migration from the initial oil core towards the interface will result from this poor compatibility issue. Migration will stop at the interface region because the poorly water-soluble drug will not migrate into the aqueous phase. The resulting increased local concentration at the interface region will trigger a supersaturation condition locally for the drug, followed by crystallization/precipitation of the active pharmaceutical ingredient that eventually leaves the formulation. The increased local concentration at the interface regions thereby causes destabilization of the formulations. Such a mechanism explains why many traditional lipid-based formulations have low loading capacity and instability issues for compound/drugs which exhibit poor water-solubility, but are only moderately hydrophobic by nature.

The systems, methods and compositions hereof provide a strategy to reduce or eliminate the difficulties of formulation problems associated with traditional amphiphilic formulations. In a number of embodiments, rationally designed amphiphilic or surfactant molecules (carrier agents) hereof bear an effective compound, drug-interacting segment or drug-interacting domain located, for example, intermediate between the hydrophilic segment or domain and the hydrophobic segment or domain (that is, at the interfacial region therebetween). The interactive segments or domains act as compound/drug interactive domains (for example, having an affinity for the compound/drug) and may, for example, be screened from a small molecule compound library. Drug interactive motifs, compounds or groups, once identified, may be incorporated into the amphiphilic agent or molecule in a modular fashion to form drug-interactive domains. For example, such domains may be installed in between a lipid or hydrophobic anchor, and a polyalkylene oxide (for example, polyethylene glycol or PEG) or other hydrophilic groups (for example, a polyvinylalcohol, a polyacrylic acid, a polyacrylamide, a polyoxazoline, or a polypeptide with, for example, charged or hydrophilic residues). The overall structure has surfactant activity with a drug-interactive domain located at the interface of water (hydrophilic) and oil (hydrophobic) phases. While potentially suitable for use with all hydrophobic or hydrophilic compounds, such a design accommodates compounds with moderate hydrophobicity or hydrophilicity better than previous formulations. In addition, polymers with branched or linear backbone configuration containing sufficient quantities of drug interactive domains as the pending groups can form complexes with drugs as well. The agents/molecules hereof have broad utility for drug molecules with diverse structures. In a number of embodiments hereof, no hydrophobic segments, regions or domains are present in the carrier agent formulations hereof. In that regard, a drug interactive domain, once identified, may be incorporated with or attached to a hydrophilic group.

Through carrier-drug interaction and time-dependent dispersion process, a regulated drug release can be achieved from drug-carrier dosing regimens in the forms of, for example, liposomes, hydrogels, granules, pellets and other physical forms. Although carrier agents hereof are discussed primarily in connection with representative examples of drugs, the carrier agents hereof are suitable for use in connection with other compounds or molecules.

In a number of embodiments, the interfacial region of an amphiphilic agent/molecule is modified (for example, enlarged and/or expanded) by inserting an interactive segment such as an amino acid or a peptide segment. Additionally, pendant groups on the amino acid or other residues may be incorporated that exhibit drug-interactive potential. Such pendant groups may, for example, be capable of π-π hydrophobic/aromatic ring stacking or hydrogen-bonding interactions to enhance the carrier-drug interaction as a way to stabilize drug formulation.

The compound/drug-interactive segment, region or domain (whether used in an amphiphilic agent hereof or in an agent hereof including the drug-interactive segment, region or domain and a hydrophilic segment, region or domain) may, for example, be experimentally determined through, for example, solubility tests of individual motifs, such as protected amino acids or PEG-conjugates of protected amino acids that have increased water solubility. The mode of detection may, for example, be visual (for example, under a microscope) for the suppression/disappearance of crystal formation, by optical density (OD) reading, by high pressure liquid chromatography (HPLC) or any other suitable measurement method for the soluble fraction of a poorly water soluble free drug that is facilitated to form nanostructure a solution in aqueous solutions. Examples of groups suitable for use in interactive segments, regions or domains hereof include, but are not limited to, fluorenylmethyloxycarbonyl (FMOC), carbobenzyloxy (Cbz or Z), and isobutoxycarbamate groups as a part of a small molecule, such as amino acid derivative that is sufficiently water soluble. The compound or a portion of the compound with which the interactive segment, region or domain is to interact can also be used in the interactive segments, regions or domains. For example, reactive groups on the compound or a portion thereof (either native to the compound/portion or created thereon by modification) can be used to bond a residue of the compound/portion within the carrier agent. Motifs immobilized on solid phase support may, for example, also be useful for the identification process by, for example, binding or absorbing a particular agent to be tested compared to the unmodified solid phase support.

The motifs may, for example, additionally or alternatively be predicted theoretically based on the known structural features of a particular agent, such as charge properties, aromatic ring structures, hydrogen bonding potential, etc. A naphthylacetyl group, for example, is predicted and experimentally confirmed to be as active as an FMOC group.

Fmoc groups, derivatives thereof and similar groups (for example, carbazoles, quinolones, isoquiolones, (9H-fluoren-9-yl)methanamine, (9H-fluoren-9-yl)methanol, 9H-fluoren-9-amine, naphthalene, and Binol) in the agents hereof have, for example, been found to be active in formulating a panel of dissimilar drugs, ranging, for example, from paclitaxel (PTX), steroids, xanthene- and porphyrin-based photodynamic agents, to hydrophobic peptide drugs, with significant improvements in both drug loading capacity and drug retention. These data suggest that groups such as Fmoc qualify as a "formulation chemophors", exhibiting a potent activity in interacting with various pharmaceutical agents and thus a capability of improving carrier-drug compatibility. Without limitation to any mechanism, the molecular basis for such interaction is believed to be the result of π-π stacking interactions between the compact fused aromatic ring structure of Fmoc units and drug (or other compound) molecules bearing, for example, one or more aromatic rings, which is normally stronger than the van der Waals interaction.

The drug-interactive motifs, groups or agents may be incorporated into, for example, a lipid-based surfactant as pendant groups (for example, peptide side-chains or pending groups) on the interactive segment (at the interface region) to form designer amphiphilic/surfactant molecules with three distinct domains: a hydrophilic head group or segment (for example, PEG), an expanded intermediate segment or interface region (interactive segment), and a hydrophobic segment, tail region or anchor region (for example, a lipid). The configuration of the motif arrangement at the interface region may, for example, be continuous or discontinuous, linear or branched. The number of lipid chains may also be varied from, for example, 0 to 4 or more.

The carrier agents hereof may thus be tailor-designed by incorporating one or more drug-interactive motifs selected based on experimental approaches and/or theoretical predictions. Once again, even hydrophilic segment-drug interactive motif conjugates without hydrophobic or lipid chains may have utility as they can form, for example, micelles, soluble complexes or form drug-loaded hydrogels, depending on the propensity of motif-motif interactions. Hydrogels may, for example, be used as topical application with slow/delayed release features.

As described above, PEG chains may be used in the hydrophilic segments hereof. PEG chains may, for example, be replaced with other hydrophilic groups, including, for example, carboxyl or amine groups that have hydrophilic properties, or other hydrophilic polymers, sugars, etc.

The carrier agents/molecules hereof, for example, may be used alone in forming micelles with a drug as an inclusion complex or may, for example, be used in mixed-micelles, as added co-surfactant, together with other lipid components to form drug-loaded micelles, emulsions, creams, liposomes, spherulites, solid-lipid nanoparticles, hydrogels, cubic phase lipogels etc. In general, the amphiphilic or surfactant carrier agents hereof act as interface stabilizers for the compound/drug to enhance formulation stability and to increase drug loading capacity.

Carrier agents hereof may also be polymeric (including hydrophobic-hydrophilic or hydrophilic repeat units) made through copolymerization, or chemical modification, with drug-interaction segments/motifs. In the case of carrier agents including a hydrophilic domain and a hydrophobic domain attached to or conjugated with the drug-interactive domain, the drug-interactive segments/motifs may be incorporated either within the hydrophobic segments or at the boundary of hydrophilic and hydrophobic segments. For example, the hydrophilic segment may be, but is not limited to a PEG or a peptide sequence enriched with hydrophilic residues or hydrophilic derivatives thereof. The hydrophobic segments may, for example, include at least one polymethylacryl group, at least one polyethylene group, at least one polystyrene group, at least one polyisobutane group, at least one polyester group, at least one polypeptide group or derivatives of any thereof. As described above, the drug interactive motif may, for example, be at least one Fmoc group (for example, as a pending group of an amino acid residue).

The agents hereof may, for example, be "drug dispensers" for oral dosing agents to, for example, enhance drug absorption in gastric or intestine fluid and/or to increase residual time. The agents may also, for example, be used to increase penetration rate for topical or mucosal applications. Moreover, the agents may also be used as colloidal formulation agents for systemic injection.

Ligands specific for cell surface molecules may, for example be incorporated into the hydrophilic segment (for example, PEG) hereof at a terminus position to facilitate the rate or specificity of cellular uptake.

In a number of embodiments, the bottom-up approach hereof begins with selecting a drug interactive domain, followed by constructing the carrier agents (for example, amphiphilic agents, surfactants or polymers), and further development into, for example, a formulation such as a micelle formulation, an emulsion formulation, a liposome formulation, a hydrogel formulation or another formulation for a specific drug. One may also use natural or synthetic molecules that contain drug/compound interactive functionality and install these molecules into surfactants to generate molecules with, for example, hydrophilic, interactive and hydrophobic orientation. Such motifs may work together with the hydrophobic domain/segment to bind/dissolve/associate with a particular agent The design principles hereof may be extended to many drugs using, for example, lipidic and polymeric systems for improved in vivo drug delivery. In that regard, the present approach provides broad utilities for formulating various types of therapeutics that are moderately hydrophobic or moderately hydrophilic and cannot be effectively formulated with traditional formulations.

For example, the utility of multi-chain PEGylated micelle-forming amphiphilic agents or surfactants for additional hydrophobic as well as hydrophilic agents has been demonstrated as set forth in the representative examples of Table 1 below. Examples of hydrophobic and bulky molecules include JP4-039, a hydrophobic, peptide-TEMPO-(2, 2,6,6-Tetramethylpiperidinyloxyl-) based stable nitroxide radical antioxidant; paclitaxel (anticancer chemotherapeutic agents); tacrolimus or FK506 (an immunosuppresent), cyclosporin A (an immunosuppresent); Eosin Y (an agent with fused aromatic ring structures used in photodynamic therapy), Rose Bengal (an agent with fused aromatic ring structures used in photodynamic therapy), protoporphyrin IX (an agent with fused aromatic ring structures used in photodynamic therapy); and epigallocatechin gallate or ECGC (green tea extract, a potent hydrophilic antioxidant and a known chemotherapy sensitizer).

The utility of single-chain PEGylated lysyl-oleylamide derivative or PEG-peptide conjugate without a hydrophobic/lipid chain for additional hydrophobic agents has, for example, been demonstrated as set forth in the representative examples of Table 2 below. Examples of hydrophobic and bulky molecules include Indomethacin (non-steroidal anti-inflammatory drug); Tamoxifen (a ligand for estrogen receptor used for endocrine (anti-estrogen) therapy for hormone receptor-positive breast); Curcumin (a herbal medicine compound that has been shown antitumor, antioxidant, antiarthritic, antiamyloid, anti-ischemic, and anti-inflammatory properties). In the case of Methoxy-PEG550-α-Fmoc-lysyl-ε-oleylamide, micelle solutions were readily prepared from drug-surfactant mixture by hydration at drug-to-surfactant ratio of 1:20 by weight. Since the drug-surfactant mixture appears to be an oil, syrup or gel, such mixtures can be packaged in soft or hard capsules, or given as syrup, or in solution. For Methoxy-PEG1000-α-Fmoc-lysyl-ε-(α-Fmoc-ε-Boc lysine), drug-carrier mixture appeared to be in the solid status before hydration. When Indomethacin-carrier complex was hydrated, it appeared to be in viscous lipogel format, which takes 30 minute to one hour to reach fully hydrated status. The slow hydration process may be useful for slow and timed release of this agent. The drug-carrier complexes for Tamoxifen and curcumin formed suspension upon hydration with a stability of ~1 hr. Additional representative studies of paclitaxel PTX loaded onto a carrier agent including only a hydrophilic segment, region or domain conjugated to a drug-interactive segment, region or domain are set forth below.

In studies with ECGC, it was discovered that despite the fact that ECGC is fairly water soluble compound in phosphate buffered saline or PBS, its multi aromatic ring structure facilitated an interaction with PEG-Fmoc4-lipopeptide and resulted in a complex that is soluble within certain drug to carrier ratios, but fell out of solution when the drug to PEG-Fmoc4-lipopeptide ratios exceeded a critical threshold. This result is a clear indication that complex formation between the two entities had occurred. Further, it was found that free ECGC in aqueous solution was readily oxidized when exposed to air into yellow colored products over 24 hrs of time after a solution was prepared in PBS, but the ECGC-lipopeptide complex prevented or slowed the oxidation reaction upon storage over a week period of time. The exact mechanism for the protection of ECGC against oxygen in the form of complex is unknown. Without limitation to any mechanism, it is believed that having the drug in a relatively hydrophobic environment that is less accessible to dissolved oxygen and the shielding effect from lipopeptides containing UV-absorbing Fmoc-groups may have contributed to the slowing of the oxidation process.

Hydrophobic agents such as vitamin E can be readily incorporated into micelles or emulsion prepared from containing PEG-Fmoc-lipopeptides. In this regard, these lipopeptides act as regular surfactants and facilitated the solubilization and formulation process of hydrophobic agents.

TABLE 1

| Tested Agents | Biologic Activities | # of ring structures | Structural features | Solubility (ug/ml) | Soluble at | Drug:carrier mole ratio | Size +/− SD (nm) |
|---|---|---|---|---|---|---|---|
| JP4-039 | antioxidant | 0 | peptiod | <1.5 | 2 mg/ml | 1:1.5 to 1:2.5 | 29.5 +/− 17 |
| Paclitaxel | Anti-neoplastic | 3 | 17-membered, tetracyclic | 0.3 | 1 mg/ml | 1:2.5 to 1:5 | 55.6 +/− 11 |
| FK506 | Immunosuppressant | 0 | 23-membered, macrolide lactone | 05/08/12 | 2.5 mg/ml | 1:1 to 1:1.5 | 62.3 +/− 9 |
| Cyclosporin A | Immunosuppressant | 0 | 11 amino acids cyclic peptide | 34.59 | 5 mg/ml | 2:1-2:1.5 | 57.3 +/− 14 |
| protoporphyrin IX | Photodynamic agent | 0 | dicarboxylixc heme | ~1 | 0.5 mg/ml | 1:6 to 1:10 | 87.2 +/− 13 |
| GW4064 | nuclear receptor FXR ligand | 3 | FXR agonist | 0.002 | >5 mg/ml | 2:1 to 1:1 | 35.4 +/− 12 |

TABLE 1-continued

| Tested Agents | Biologic Activities | # of ring structures | Structural features | Solubility (ug/ml) | Soluble at | Drug:carrier mole ratio | Size +/− SD (nm) |
|---|---|---|---|---|---|---|---|
| Rose Bengal | Photodynamic agent | 3 | carboxylic stilbene isoxazoles | freely soluble | >5 mg/ml | 2.5:1 to 2:1 | 101.6 +/− 7 |
| EGCG | Green tea extract, antioxidant | 4 | polyphenol | freely soluble | 5 mg/ml | 2.5:1 | 89.9 +/− 12 |

TABLE 2

| Tested Agents | Methoxy-PEG550-α-Fmoc-lysyl-ε-oleylamide (20 mg/ml) | Methoxy-PEG1000-α-Fmoc-lysyl-ε-(α-Fmoc-ε-Boc lysine), 20 mg/ml |
|---|---|---|
| Curcumin | 1 mg at 1 mg/ml, micelle solution | 1 mg at 1 mg/ml, viscous gel |
| Indomethacin | 1 mg at 1 mg/ml, micelle solution | 1 mg at 1 mg/ml, fine suspension |
| Tamoxifen | 1 mg at 1 mg/ml, micelle solution | 1 mg at 1 mg/ml, suspension |

Figure 3A:
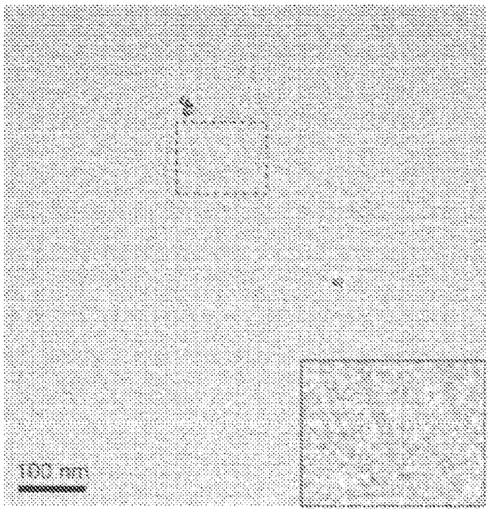
FIG. 3A illustrates a cryo-EM images of lipopeptide 4 micelles.
Figure 3B:
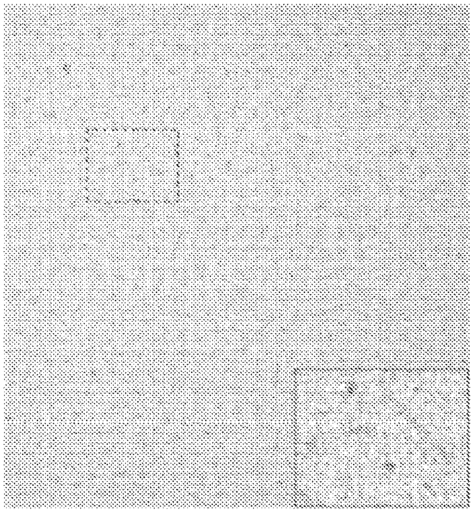
FIG. 3B illustrates a cryo-EM images of lipopeptide and JP4-039-lipopeptide complexes.
Figure 3C:
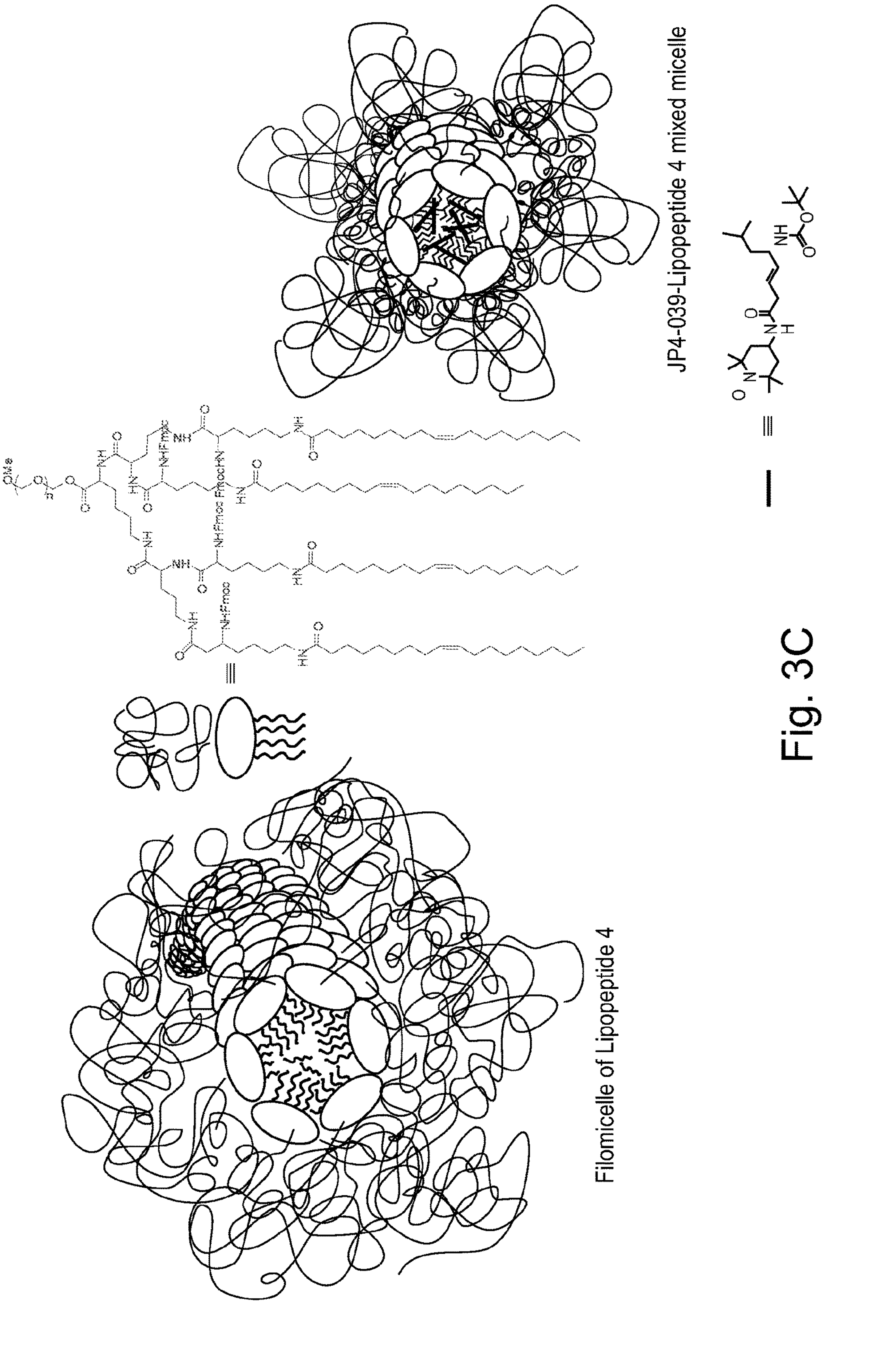
FIG. 3C illustrates a proposed, idealized model for lipopeptide micelles and drug-lipopeptide complexes.

As described above, a number of representative examples of formulations hereof include emulsion and micelle formulations for the hydrophobic nitroxide radical antioxidant JP4-039 (see, for example, FIG. 3C). In the case of JP4-039, a drug-interactive domain was identified from a panel of protected amino acid derivatives. In that regard, because JP4-039 possesses peptide characteristics to some degree, we searched for structural elements that might interact with JP4-039 from amino acid derivatives. Special attention was paid to lysine in representative studied, because it has three orthogonally protected functional groups that can simplify the subsequent conjugation maneuver.

Dilution of an alcoholic solution of JP4-039 with saline instantaneously triggers crystal formation as a result of limited water solubility and high crystalline properties of this compound. We identified several readily available amino acid derivatives with different N-protecting groups that are capable of inhibiting the crystallization of JP4-039 in aqueous solution. Microscopic studies indicated one of the lysine derivatives effectively reduced the size as well as the number of JP4-039 crystals in saline in a dose-dependent manner, and eventually completely eliminated the formation of JP4-039 crystals at sufficient quantities. In several studies, we compared a group of ε-Boc-lysine derivatives bearing various modifying groups on the α-$NH_2$ position. Based on the ability of crystal inhibition at varied molar ratios, the amino acids with the bulkiest Fmoc were found to be the most potent, followed by the amino acids with midsized iso-butyloxycarbonyl and benzyloxycarbonyl (Cbz) groups, while the amino acids with compact t-Boc and the smallest acetyl group were the least effective (Table 3). FIG. 1 illustrates structures of various amino acid derivatives studied in solubility studies of JP4-039 in Table 3. We replaced the free carboxyl group of α-Fmoc-ε-Boc-lysyl with a methoxy $PEG_{1000}$ as an ester and found that it still maintained the full capacity of the free acid derivative (not shown). In Table 3, the followings designations are used: U-Initially soluble but unstable after 5 min; V-forming vesicles; I-insoluble; and S-soluble.

TABLE 3

| Molar ratios | 5 | 10 | 20 | 30 | 40 | 50 |
|---|---|---|---|---|---|---|
| Boc-Phe-OH | U | U | U | U | U | V |
| Cbz-Tyr-OH | V | U | U | U | U | V |
| Cbz-(Isb)-Lys-OH | V | V | V | V | V | V |
| Di-(tBoc)-Lys-OH | V | V | V | V | V | V |
| Cbz-β-Ala-OH | I | I | I | I | I | I |
| tBoc-(Cbz)-Lys-OH | I | I | I | I | I | S |
| Cbz-(tBoc)-Lys-OH | I | I | I | I | S | S |
| Di-(Cbz)-Lys-OH | I | I | S | S | S | S |
| Isb-(Cbz)-Lys-OH | I | S | S | S | S | S |
| Fmoc-(tBoc)-Lys-OH | S | S | S | S | S | S |
| Ace-(Cbz)-Lys-OH | I | I | I | I | I | S |
| CBz-(Ace)-Lys-OH | I | I | I | I | I | S |
| Benz-Phe-OH | I | U | U | U | U | S |

Of the groups in the representative studies of Table 3, we experimentally identified Fmoc amine-protecting group as the most potent drug-interactive group for JP4-039. α-Fmoc-ε-tBoc protected lysine is a readily available amino acid derivative widely used for solid phase peptide synthesis. Moreover, in has been indicated that dipeptides carrying such group may have intrinsic anti-inflammatory activity.

Figure 2:
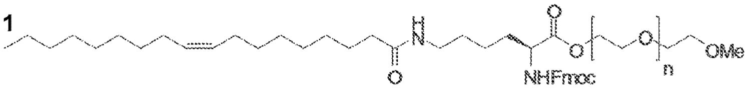
FIG. 2 illustrates chemical structures of PEG-lipid and PEG-lipopeptide conjugates used in a number of representative studies of JP4-039 hereof.
Figure 2:
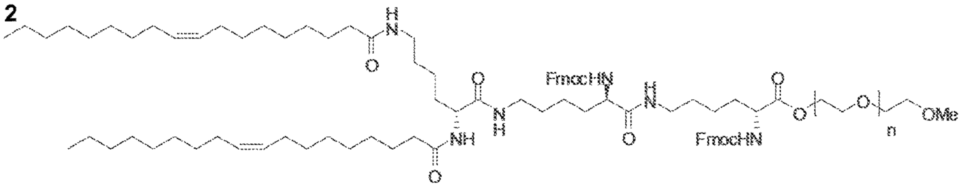
Figure 2:
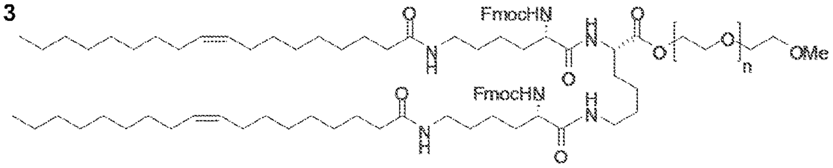
Figure 2:
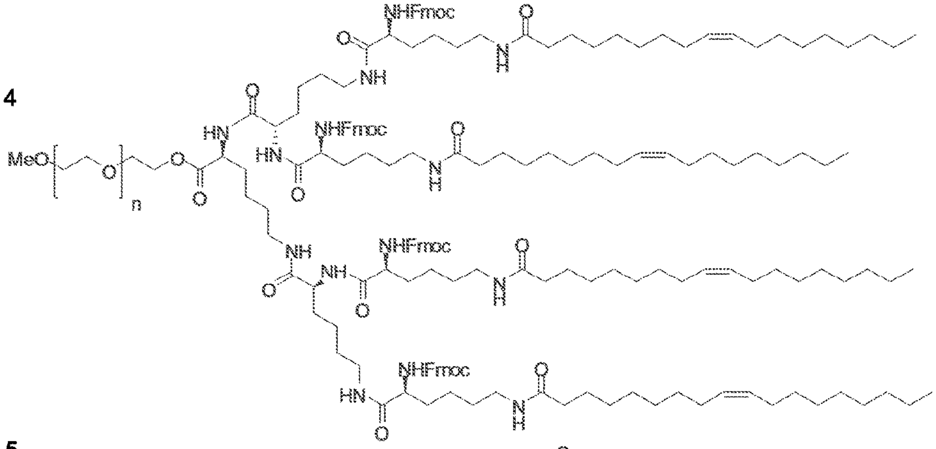
Figure 2:
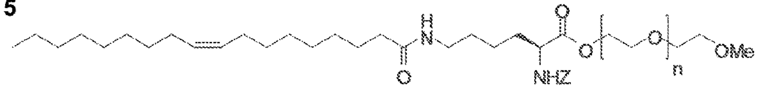
Figure 2:
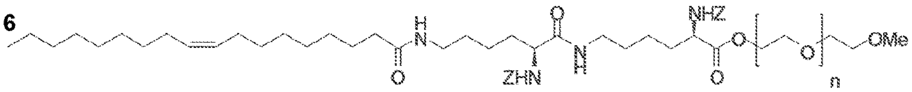
Figure 2:
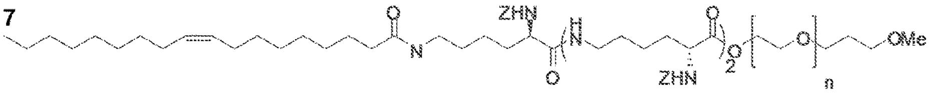
Figure 2:
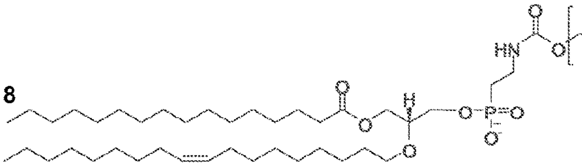
Figure 2:
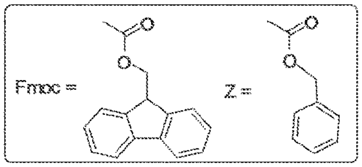

Seven PEG-lipopeptides carrying varied numbers of α-Fmoc or α-Cbz lysine residues at the interface region and a control PEG-lipid conjugate were synthesized as illustrated in FIG. 2. The single chain PEG-lipoamino acid derivative 1 was synthesized by first esterifying monomethoxy PEG-OH with α-Fmoc-ε-Boc-lysine, followed by deprotection of the t-Boc group, then end-capped with oleic chloride. A double chain lipopeptide with two consecutive α-Fmoc-lysine residues was made by end capping of monomethoxy PEG-α-Fmoc-lysyl-α-Fmoc-ε-$NH_2$-lysine with an α,ε-dioleoyl lysine to obtain PEG-lipopeptide 2. PEG-lipopeptide 3 and 4 were prepared by end-capping monomethoxy PEG-lysine conjugates carrying two or four α-Fmoc-lysyl groups attached through one or three lysine bridges with oleic chloride. The long chain lipid tails enable these PEG derivatives to associate tightly with each other in micelles, or anchor to emulsion or liposome formulations with additional lipid components. Additional single lipid chain methoxy-PEG-lipopeptides containing 1-3 consecutive α-Cbz-lysyl groups (PEG-lipopeptide 5-7) were similarly synthesized. Methoxy-$PEG_{2,000}$-carbamoyl-POPE (8) was synthesized by reacting palmitoyl oleoyl phosphatidyl ethanolamine with methoxy-$PEG_{2,000}$ activated with phosgene according to a published methodology.

Particle size measurement by dynamic light scattering method for α-Fmoc-ε-tBoc-lysine prepared in 0.1 M $KHCO_3$ revealed that the majority of particles had measured diameters between 2-5 nm, which indicates these are micelles. All PEG lipid and lipopeptide conjugates readily formed a transparent dispersion in water, with the suspension made from PEG-lipopeptides containing α-Fmoc-lysyl units showing significantly increased viscosity, suggesting the presence of elongated, worm-like micellar assemblies (filomicelles) that self-entangle with each other. Measured critical micelle concentration (CMC) values of 3.4-6.8 μM are in a range that is comparable to those reported for nonionic surfactants with long aliphatic chains (Table 4).

TABLE 4

| PEG-lipopeptides | Drug:carrier ratio for solubilization (mol:mol) | CMC (μM) | Particle Sizes w/o JP4-039 (nm) | Particle Sizes w/JP4-039 (nm) |
|---|---|---|---|---|
| $PEG_{2000}$-FmocLys-Oleate | 1:10.7 | 5.0 | Not done | Not done |
| $PEG_{2000}$-Lys(FmocLys-Oleate)$_2$ | 1:5.0 | 4.2 | 106.7 +/− 2.5 | 94.2 +/− 1.7 |
| $PEG_{1000}$-FmocLys-FmocLys-Lys-di-Oleate | 1:6.3 | Not done | Not done | Not done |
| $PEG_{5000}$-Lys[Lys(FmocLys-Oleate)$_2$]$_2$ | 1:1.5 | 3.4 | 132.1 +/− 8.5 | 128.6 +/− 5.9 |

Methoxy PEG lipopeptide derivatives containing varied numbers of Fmoc and oleoyl groups were active in solubilizing JP4-039 in saline at a 1:1.5 to 1:15 drug-to-carrier molar ratios. Based on the minimal molar ratio between carrier and drug that is required to form soluble mixed micelles, the conjugate carrying tetra-α-Fmoc-lysyl groups (4) is more efficient than the conjugates 2 and 3 containing two Fmoc lysyl groups, while the mixed micelles formed with the conjugate 1 containing mono-Fmoc lysyl group were unstable over time (Table 4).

Figure 4:
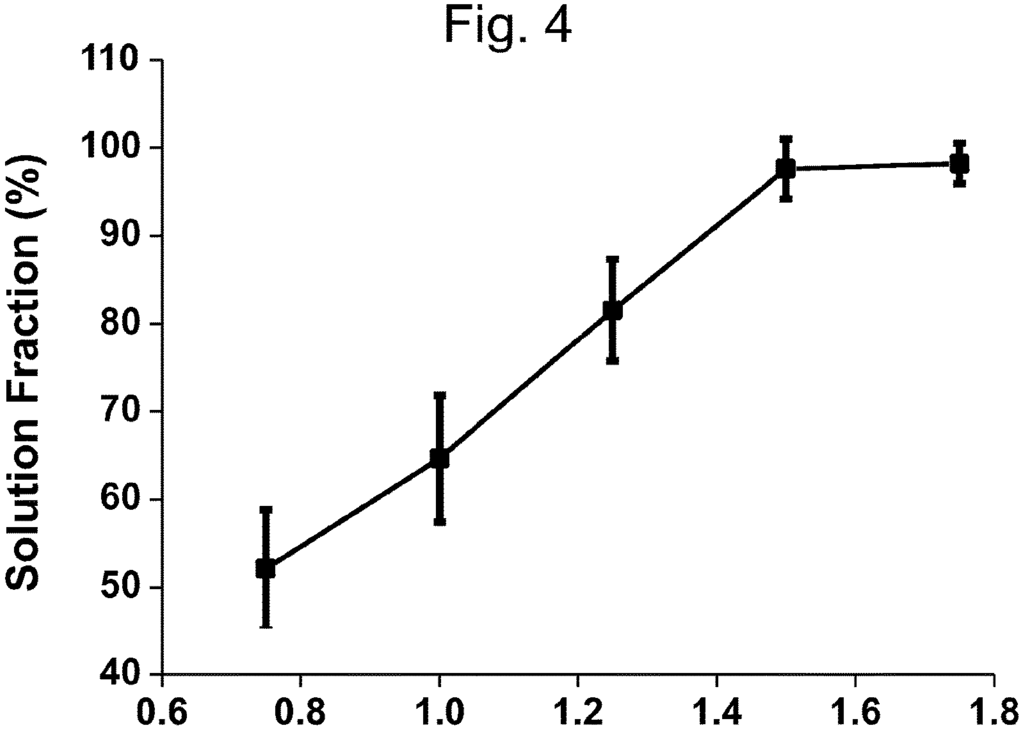
FIG. 4 illustrates a study of solubilization of JP4-039 facilitated by PEG-lipopeptide 4 micelles.

Given sufficient carrier-to-drug ratios, PEG-lipopeptide 4 was effective in maintaining a stable formulation for a prolonged period of time (>one month) during which no sign of crystal formation was noticed. A dose-dependent solubilization relationship was established for lipopeptide 4 and a fixed amount of JP4-039, with a minimal carrier-to-drug molar ratio around 1.6:1 (see FIG. 4). In contrast, comparable PEG-α-Cbz-lysyl lipid conjugates at these ratios could only slow down the crystallization of JP4-039, but failed to form a stable JP4-039-containing micelle solution (not shown). Methoxy-$PEG_{2,000}$-carbamoyl-POPE 8, a control micelle forming-PEG-lipid conjugate that lacks lysyl domain, was inactive at comparable molar ratios (not shown).

An Fmoc group contains a bulky, fused fluorenylmethyl ring structure capable of providing strong hydrophobic and π-π stacking interactions with other aromatic moieties, including itself. The carbamoyl bond that links the ring structure to lysine can also provide hydrogen-bonding capacity. Fmoc promotes parallel interactions of individual short peptides carrying the same group which often leads to the formation of elongated nano-assemblies. Examples include Fmoc-containing short peptides that form interconnected tubular structures and turn into hydrogels, and lipopeptides 3 (not shown) and 4 (see FIGS. 3A and 3B). Without limitation to any mechanism or model, the fact that an excess of α-Fmoc-ε-Boc-lysine and α-Fmoc-lysyl-containing lipopeptide conjugates are required to solubilize JP4-039 suggests a model that involves one JP4-039 surrounded by several Fmoc-containing compounds held together through a combination of hydrogen bonding, hydrophilic and hydrophobic cooperative interactions among the drug-carrier, and carriers themselves (see FIG. 3C). Lipopeptide 4, which has four Fmoc-groups arranged in a constraint manner at the interface and has a high local concentration of Fmoc groups, requires the lowest molar ratio of carrier to drug to achieve a complete solubilization (see Table 4 and FIG. 4) and provide the best performance of the studied groups. In the solubilization studies of FIG. 4, various amounts of tetra chain $PEG_{5,000}$-lysyl-[lysyl-(α-Fmoc-ε-oleyol-lysine)$_2$]$_2$ were mixed with JP4-039 in $CHCl_3$ followed by solvent evaporation, the drug-loaded micelles were prepared by hydration in saline. The amounts of solubilized JP4-030 were determined by $OD_{448}$ measurements from supernatant.

Figure 5:
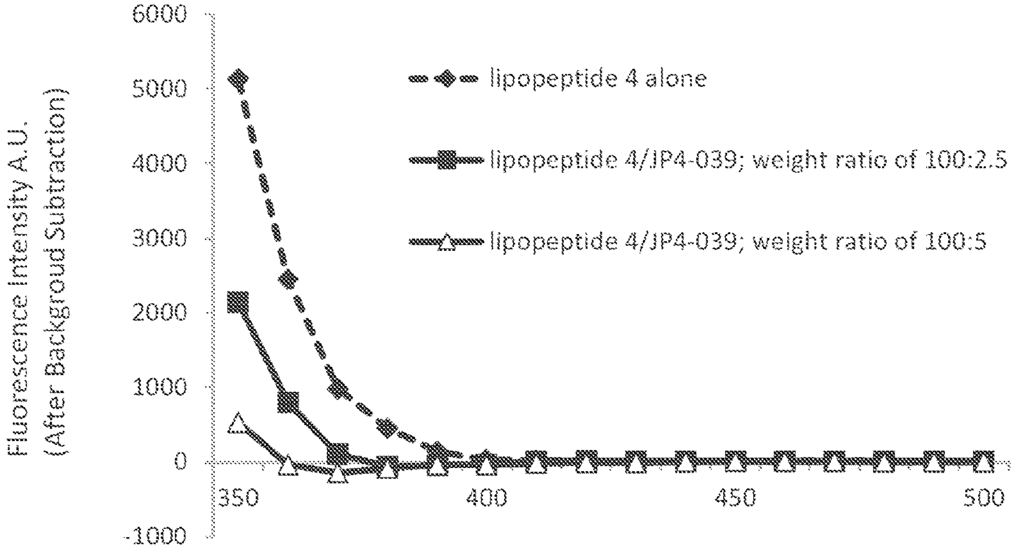
FIG. 5 illustrates the results of fluorescence quenching studies of lipopeptide 4 alone (-♦-) and lipopeptide 4 with JP4-039 at weight ratios of 100:2.5 (-■-) and 100:5 (-▲-).

The above-described model of Fmoc-JP4-039 interaction was supported by our fluorescence quenching studies. In that regard, to demonstrate that drug and carrier molecules are physically associated with each other in mixed micelles, we studied the group-group interactions using fluorescence quenching assay. FIG. 5 shows the fluorescence spectra of intrinsic fluorescence originating from Fmoc-groups of lipopeptide 4 (at an excitation wavelength of 300 nm) in the absence JP4-039 (-◆-) and lipopeptide 4 with JP4-039 at weight ratios of 100:2.5 (-■-) and 100:5 (-▲-). A large scale quenching effect was recorded when JP4-039 was added at a drug/carrier molar ratio of 1:4~5. The electron-rich nitroxide group is known to be a strong fluorescent quencher for 5-carboxytetramethylrhodamine (5-TAMRA) when placed in close distance to 5-TAMRA-labeled short DNA. Our data therefore indicated that JP4-039 is in a close distance from the Fmoc-groups in lipopeptide 4 micelles. We also conducted 2-D nuclear magnetic resonance (NMR) spectroscopy to further confirm the interaction between Fmoc and JP4-039. The results indicated that JP4-039 is contained and surrounded by the Fmoc groups within the micelle assemblies, where it has closer distance to the ring structures than the rest of molecules.

Fmoc may not be the only group involved in the carrier-drug interaction in JP4-039-loaded micelles. Cryo-EM images show that the drug-loaded micelles have apparent electron-dense region throughout the visible structures, while in empty tubular micelles the core region is electron-light, which would suggest that either JP4-039 molecules may be incorporated into regions that contain both interface and lipid portions through the extensive re-organization process, or alternatively, the dark appearance could be simply as a result of the projected image of relatively dense shell made of JP4-039 distributed along the interfacially located Fmoc groups.

Figure 6:
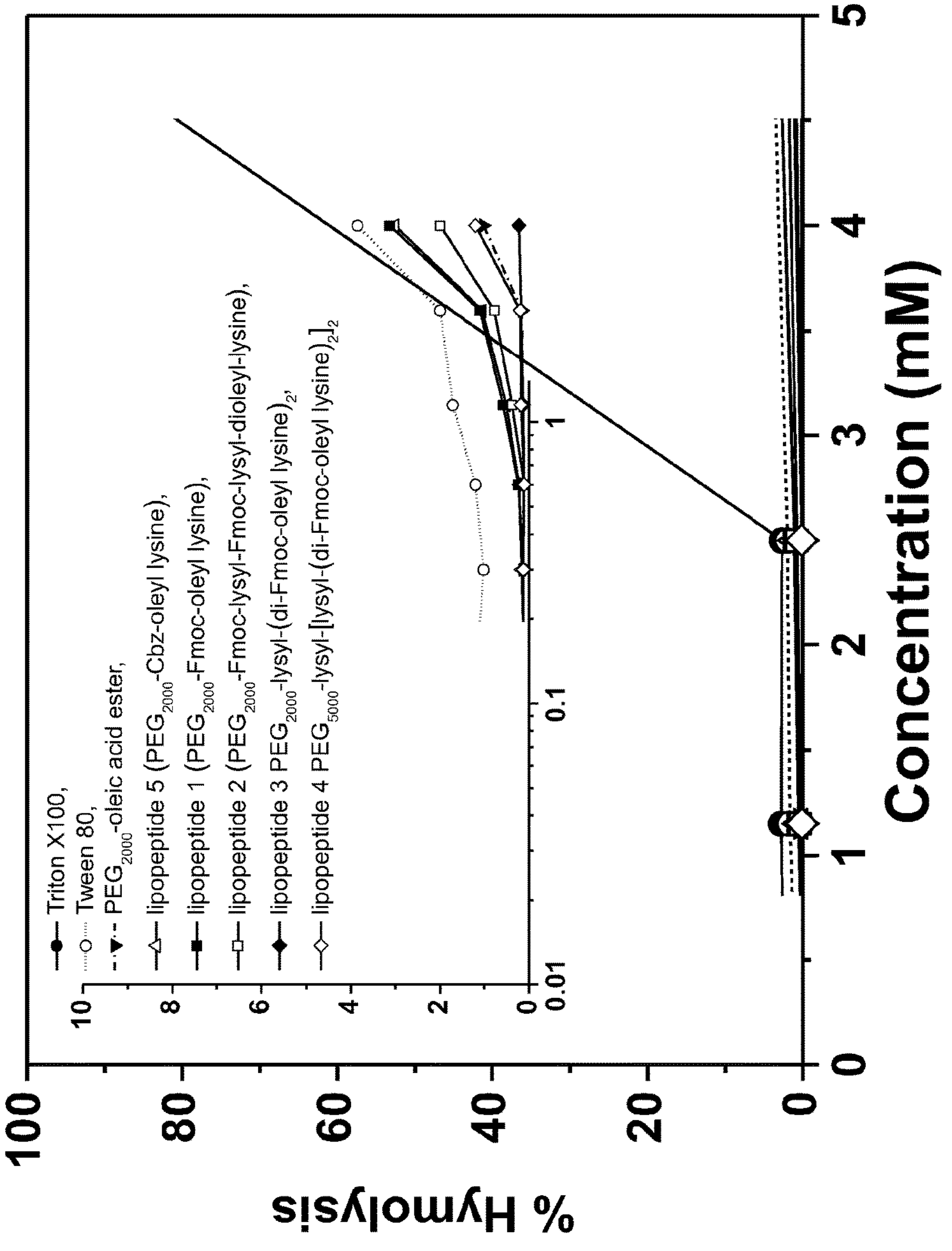
FIG. 6 illustrates a comparison of hemolytic activity of surfactants on rat red blood cells for -●-Triton X100, "○" Tween 80, -▼- $PEG_{2000}$-oleic acid ester, -Δ- lipopeptide 5 ($PEG_{2000}$-α-Cbz-ε-oleyl lysine); -■-, lipopeptide 1($PEG_{2000}$α-Fmoc-ε-oleyl lysine), -□-, lipopeptide 2 ($PEG_{2000}$α-Fmoc-lysyl-α-Fmoc-lysyl-ε-dioleyl-lysine), -♦-, lipopeptide 3 [$PEG_{2000}$-lysyl-(α,ε-di-Fmoc-ε-oleyl lysine)$_2$, and -◇-, lipopeptide 4 $PEG_{5000}$-lysyl-[lysyl-(α,ε-di-Fmoc-ε-oleyl lysine)$_2$]$_2$.

We also examined the hemolytic activity of plain micelles prepared from PEG-lipid and lipopeptide conjugates on rat red blood cells and compared the results to two widely used ethoxylated nonionic surfactants: Triton X-100 and Tween 80. In the studies of FIG. 6, rat red blood cells (1%) were incubated with surfactants at indicated concentrations for 2 hrs at 37° C. After such incubation, supernatants were carefully withdrawn, measured for at $OD_{540}$ nm, and calculated based on OD value under a condition that total hemolysis occurred. As shown in FIG. 6, while Triton X-100 showed 100% hemolysis at 5 mM, no significant hemolysis (≤2%) was noticed at or below this concentration for Tween 80 and all the PEG-lipid conjugates reported in this work.

Figure 7:
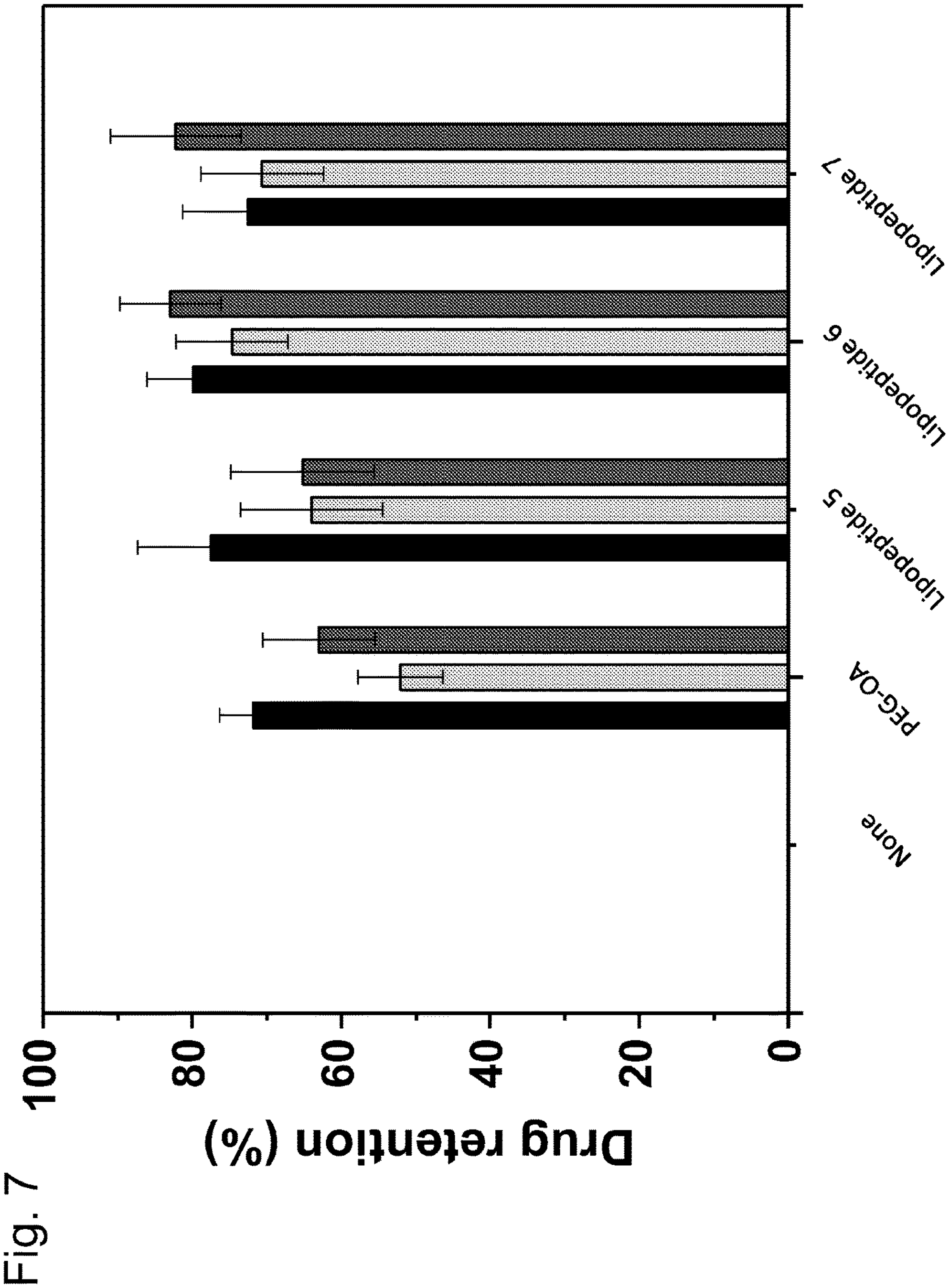
FIG. 7 illustrates the effect of co-surfactant on colloidal stability and drug loading capacity of sesame oil-egg PC emulsion containing JP4-039, wherein the rates of drug incorporation for freshly prepared (black bars) and on day 7 (light grey bars) for sesame oil-egg PC emulsion (SOPC), SOPC with 20% PC replaced with PEG-OA, lipopeptides 5, 6, 7 were determined after retrieval of JP4-039 from these formulations, and the % of initial (dark grey bars) were calculated from these data (data were presented as mean±SD (n=3)).
Figure 8:
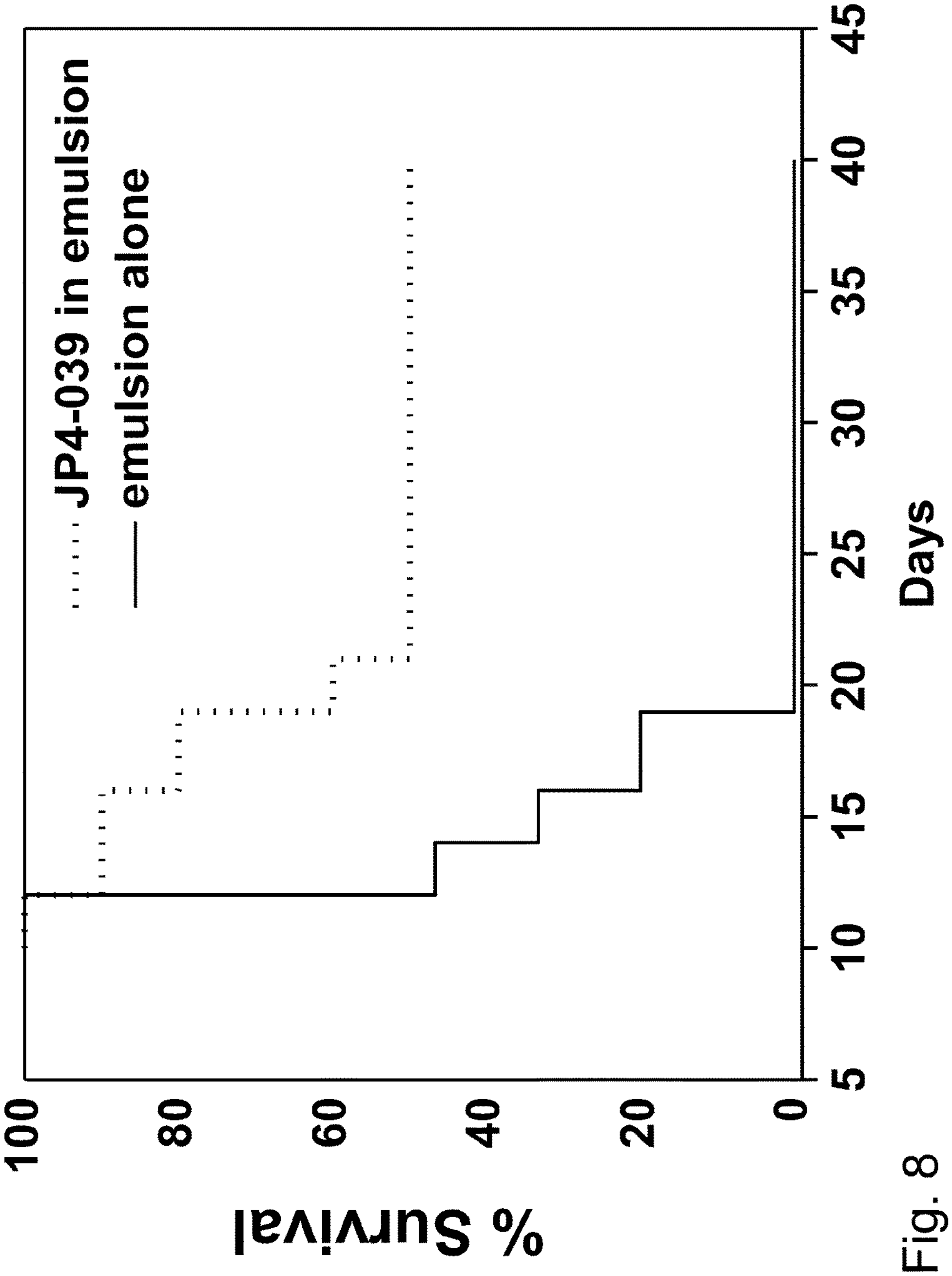
FIG. 8 illustrates studies of in vivo radiation mitigation activity of JP4-039 formulated in emulsion against whole body irradiation in mice, wherein the mice were injected i.p. with emulsion alone (solid circles) or JP4-039 formulated in emulsion (open circles, 20 mg/kg, 24 h after irradiation).

In a number of embodiments, one or more co-surfactant may be used to stabilize drug-loaded emulsions hereof. In contrast to the good solubilizing activity of α-Fmoc-lysyl containing lipopeptides as stand-alone micelle formulations for JP4-039, lipopeptides containing one to three α-Cbz-lysyl groups in linear configuration failed to form stable mixed-micelles with JP4-039 (not shown). However, we found that they acted as co-surfactants and stabilized the soy phosphatidyl choline-sesame oil emulsion formulation which we have previously found to have poor retention properties for JP4-039 over time (see FIG. 7). About 15~30% of drug were dissociated from the emulsions (with and without pegylation) 7 days following the preparation. The drug retention rates were significantly improved when 20% mole of soy phosphatidyl choline was replaced with equal amounts of one of the lipopeptides containing α-Cbz-lysyl. Moreover, the added co-surfactant also speeded up the emulsion preparation by sonication. When given to animals by single injection via i.p. route 24 h after the exposure to a lethal dosage of irradiation, JP4-039 formulated in the improved emulsion formulation showed significant radiation protective effects and improved animal survival (both survival time and overall survival rate) over the control group (see FIG. 8), confirming that JP4-039 formulated in these formulations are pharmacologically active in vivo. FIG. 8 illustrates in vivo radiation mitigation activity against whole body irradiation in mice: In the studies of FIG. 8, all mice were irradiated with a total-body dose of 9.5 Gy at a dose rate of 0.8 Gy/min. The mice were injected i.p. with emulsion alone (solid circle) or JP4-039 formulated in emulsion (open circle, 20 mg/kg, 24 h after irradiation). Mice were followed until they have lost 20% of their body weight or appear moribund, at which time they are euthanized.

The systems described above are very practical. In that regard, both amino acid derivatives and PEGs are readily available in high purity. Chemistries involved in Fmoc and t-Boc protection/deprotection and coupling are all well studied and one can have the flexibility in introducing the motif of choice at the interface region. A highly efficient polymer-assisted liquid phase synthesis scheme was adopted to prepare gram quantities of PEGylated lipopeptides without having to use chromatographic purification steps. The modular design allows one to generate a series of compounds that share the similar general structure and self-assembly properties, yet with the flexibility to change motifs at the interface region. Finally the stepwise process allows a smooth translation from identification of drug-interacting group, tailor-designed surfactant synthesis, to micelle, liposome or emulsion-based drug formulation system. The process described above in connection with JP4-039 can be easily extended to the development of various types of new lipidic and polymeric systems for improved in vivo delivery of therapeutic agents other than JP4-039.

For example, Table 5 demonstrate that inclusion of a drug-interactive domain (Fmoc) significantly improves the paclitaxel or PTX loading capacity and the stability of PTX loaded $PEG_{5000}$-Fmoc-$FTS_2$ and $PEG_{5000}$-FTS micelles, wherein FTS designates a farnesylthiosalicylate group.

TABLE 5

| Micelles | Molar ratio | Conc. of PTX [a] (mg/mL) | Size [b] (nm) | PDI[c] | DLC [d] (%) | DLE [e] (%) | Stability [f] (hour) |
|---|---|---|---|---|---|---|---|
| $PEG_{5K}$-$FTS_2$ | — | — | 17.6 | 0.20 | — | — | — |
| $PEG_{5K}$-$FTS_2$:PTX | 2.5:1 | 1 | 24.9 | 0.35 | 5.5 | 81.2 | 2 |
| $PEG_{5K}$-$FTS_2$:PTX | 5:1 | 1 | 25.6 | 0.23 | 2.8 | 97.6 | 20 |
| $PEG_{5K}$-Fmoc-$FTS_2$ | — | — | 24.8 | 0.22 | — | — | — |
| $PEG_{5K}$-Fmoc-$FTS_2$:PTX | 0.5:1 | 1 | 36.2 | 0.19 | 21.8 | 55.4 | 12 |
| $PEG_{5K}$-Fmoc-$FTS_2$:PTX | 1:1 | 1 | 29.4 | 0.11 | 12.3 | 73.2 | 15 |
| $PEG_{5K}$-Fmoc-$FTS_2$:PTX | 2.5:1 | 1 | 29.7 | 0.12 | 5.3 | 87.3 | 17 |
| $PEG_{5K}$-Fmoc-$FTS_2$:PTX | 5:1 | 1 | 25.9 | 0.27 | 2.7 | 96.0 | 48 |

Figure 9A:
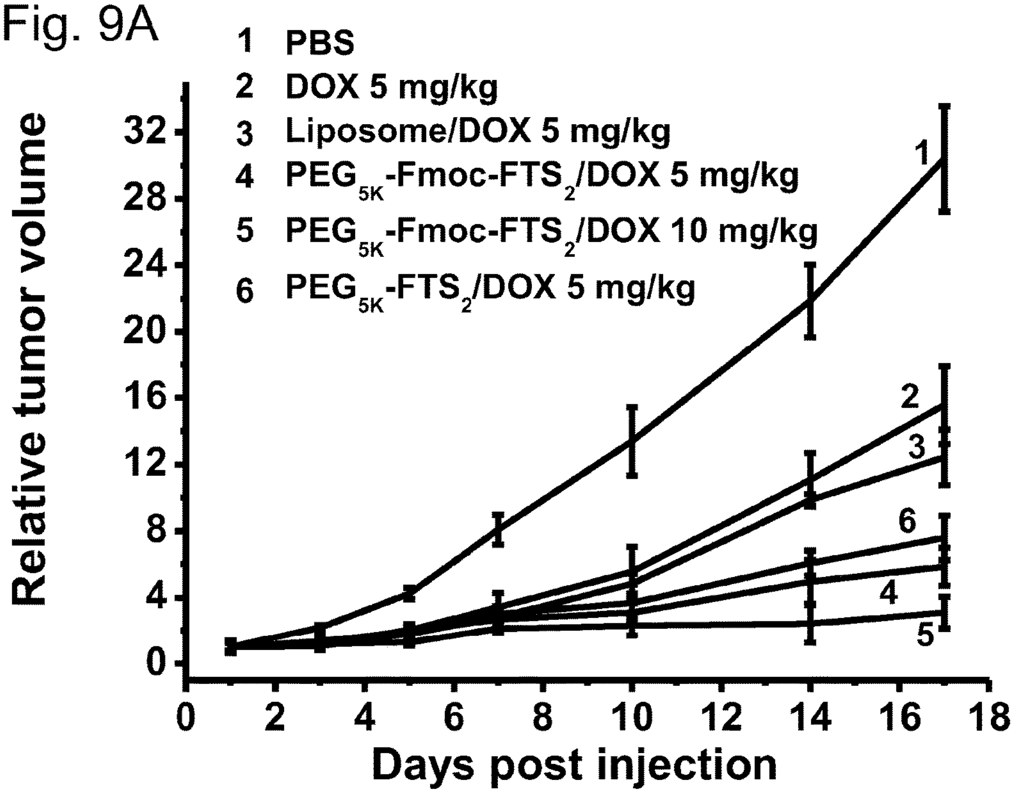
FIG. 9A illustrates enhanced antitumor activity of Doxorubicin or DOX formulated in $PEG_{5k}$-Fmoc-$FTS_2$ micelles represented by changes of relative tumor volume.
Figure 9B:
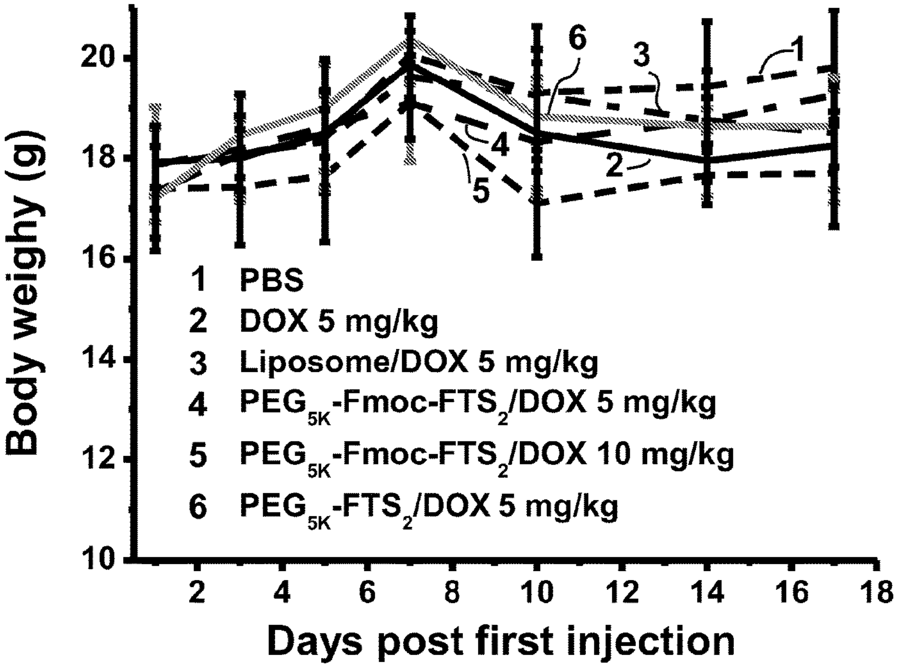
FIG. 9B illustrates body weight changes after administration of DOX formulated in $PEG_{5k}$-Fmoc-$FTS_2$ micelles.

Likewise, FIGS. 9A and 9B illustrate enhanced antitumor activity of Doxorubicin or DOX formulated in $PEG_{5k}$-Fmoc-$FTS_2$ micelles. FIG. 9A illustrates changes of relative tumor volume, while FIG. 9B illustrates body weight changes after administration. In the studies of FIGS. 9A and 9B, a syngeneic murine breast cancer model (4T1.2) was used to examine the therapeutic effect of different formulations of DOX. Mice were randomly divided into eight groups (n=5) and administered i.v. with PBS (control), DOX (5 mg DOX/kg), Liposome/DOX (5 mg DOX/kg), DOX-loaded $PEG_{5K}$-Fmoc-$FTS_2$ micelles (5, 10 mg DOX/kg), and DOX-loaded $PEG_{5K}$-$FTS_2$ (5 mg DOX/kg), respectively on days 1, 4, and 7. Tumor sizes were measured with digital caliper three times a week. The body weights of all mice from different groups were measured every three days.

Data in Table 6 demonstrate that inclusion of the drug-interactive domain Fmoc also significantly improves DOX loading capacity of PEG-Vitamin E-based micellar system. In Table 6, the following designations are used: PEG-$VE_2$—PEG-Vitamin $E_2$—PEG-$FVE_2$: PEG-Fmoc-Vitamin $E_2$; DLC—loading capacity; and DLE—loading efficiency.

TABLE 6

| Micellar formulations | Molar ratios | Size (nm) | DLC (%) | DLE (%) |
|---|---|---|---|---|
| PEG-$VE_2$:DOX | 2:1 | 22.4 ± 0.9 | 4.3 | 84.3 |
| PEG-$FVE_2$:DOX | 0.1:1 | 61.4 ± 2.3 | 45.5 | 79.5 |
| | 0.2:1 | 53.6 ± 1.5 | 30.6 | 86.4 |
| | 0.5:1 | 51.1 ± 2.1 | 14.3 | 96.3 |

Figure 10A:
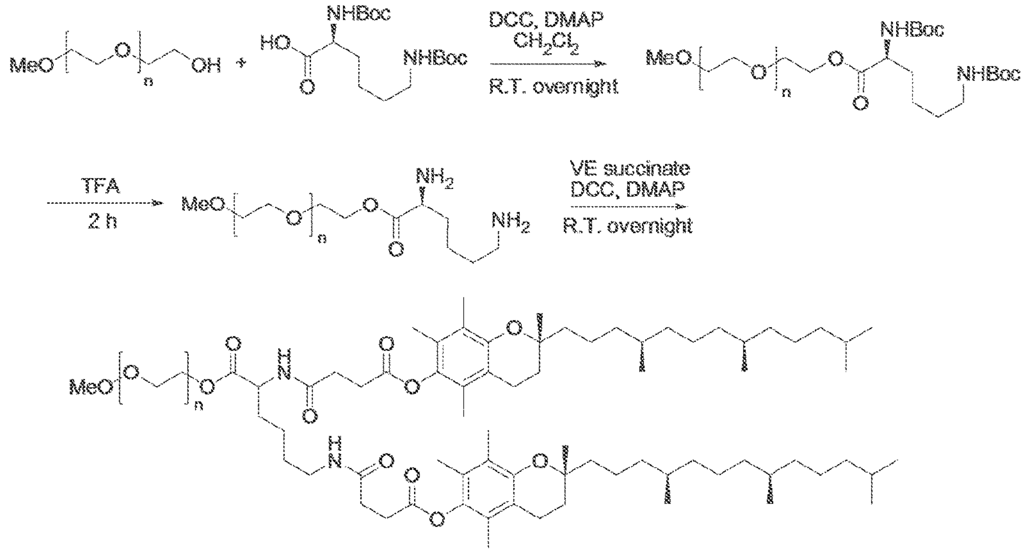
FIG. 10A illustrates synthesis of $PEG_{5000}$-$VE_2$ (PEG-$VE_2$), wherein VE represents Vitamin E.
Figure 10B:
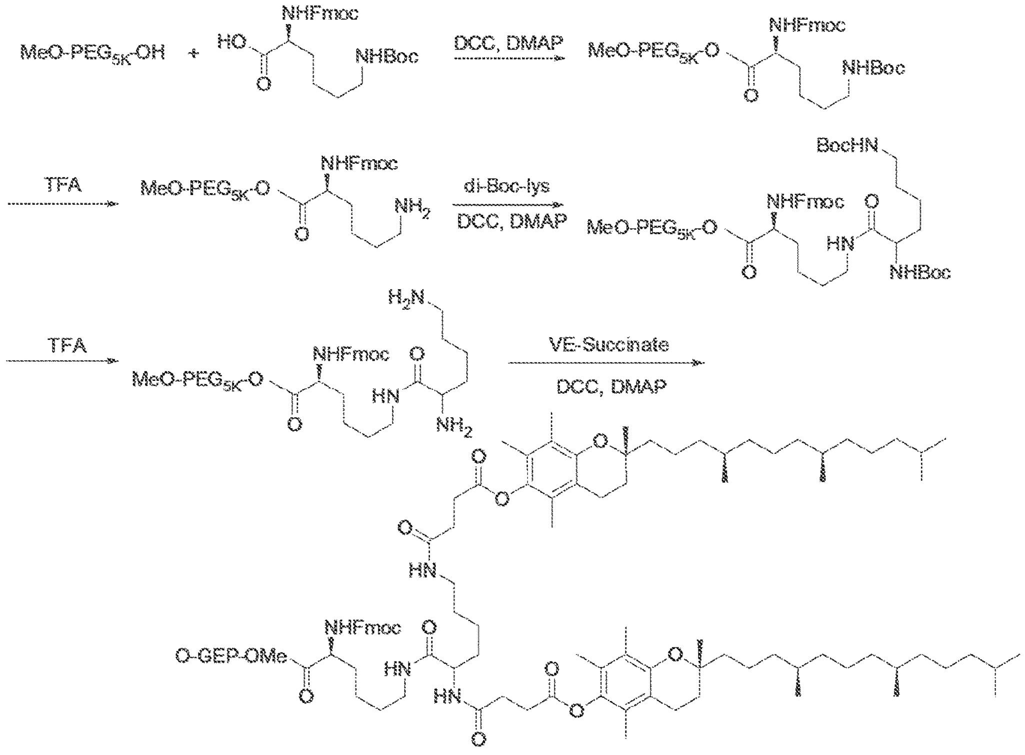
FIG. 10B illustrates synthesis of $PEG_{5000}$-Fmoc-$VE_2$ (PEG-$FVE_2$).
Figure 11:
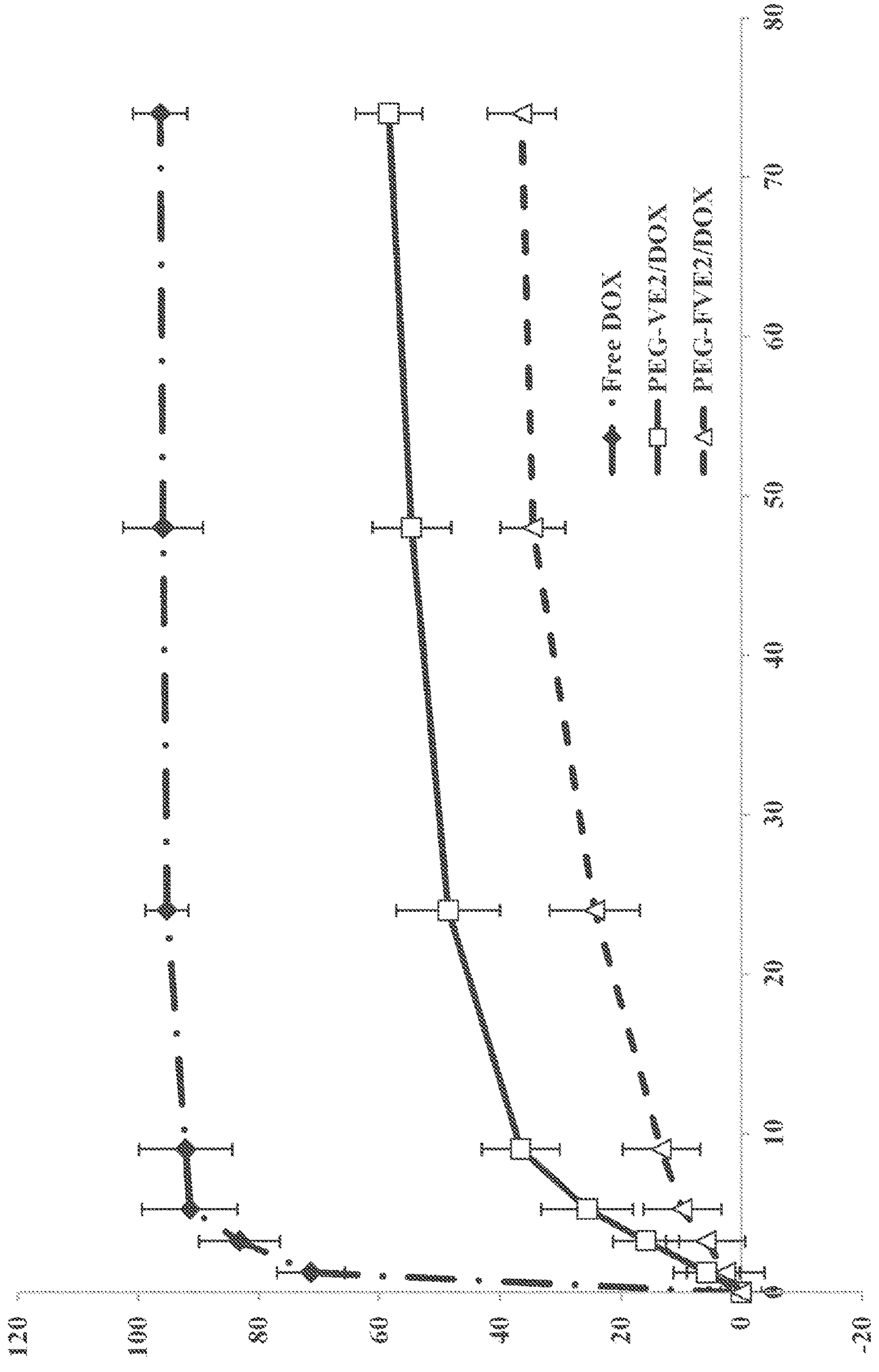
FIG. 11 illustrates a study of the kinetics of release in a dialysis assay for DOX formulated in PEG-$FVE_2$ micelles exhibited a slow.
Figure 12:
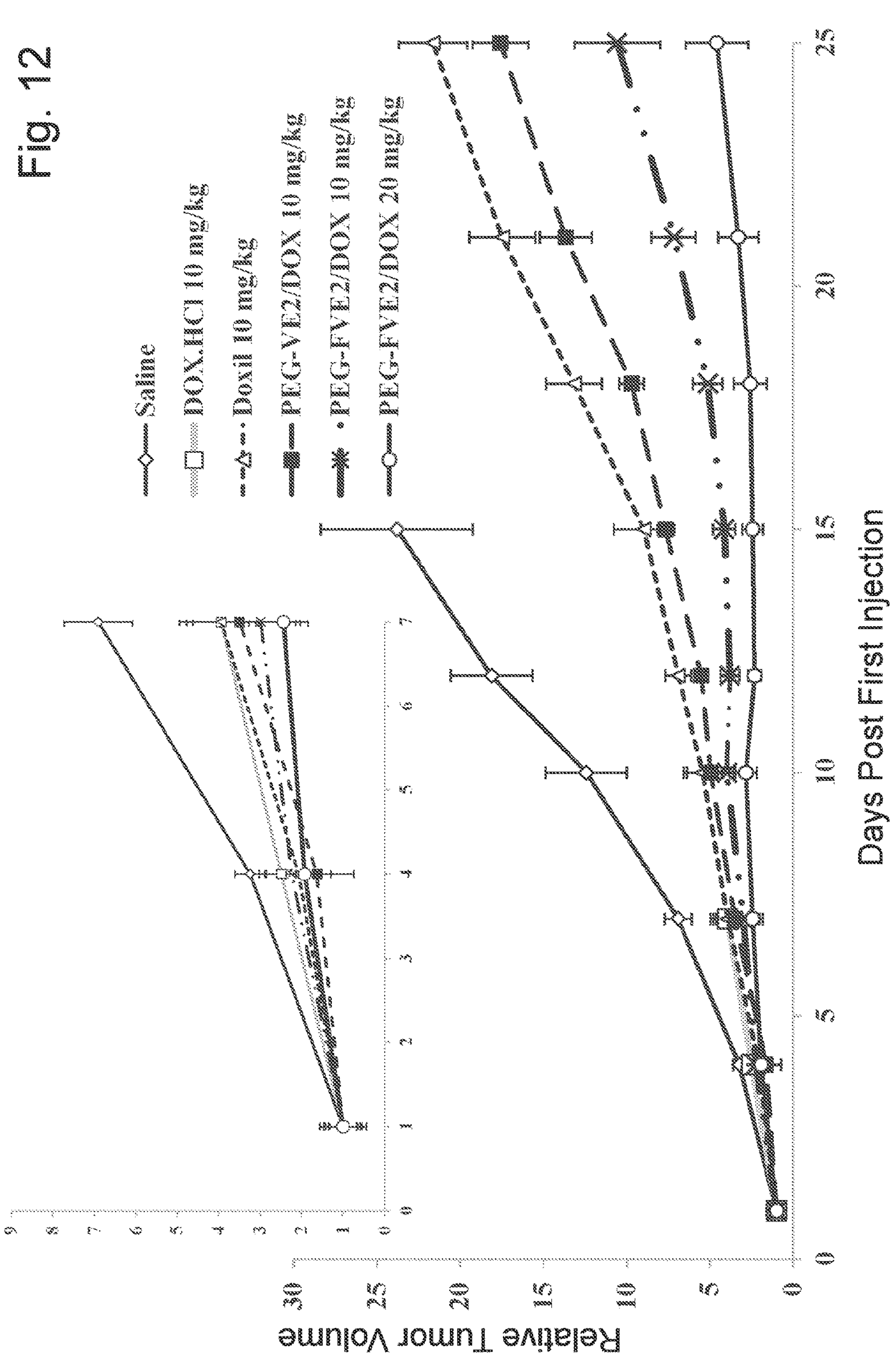
FIG. 12 illustrates that DOX formulated in PEG-$FVE_2$ micelles show superior antitumor activity over free DOX or DOXIL® (a doxorubicin HCl liposome injection available from Janssen Biotech, Inc. of Horsham, Pa.) in an s.c. murine breast cancer model (4T1.2) ($P<0.01$ (vs. PEG-$VE_2$/DOX at 10 mg/kg); $P<0.001$ (vs. DOXIL)).

FIG. 10A illustrates synthesis of $PEG_{5000}$-$VE_2$ (PEG-$VE_2$) and FIG. 10B illustrates synthesis of $PEG_{5000}$-Fmoc-$VE_2$ (PEG-$FVE_2$), which are further described in the Experimental section set forth below. As illustrated in FIG. 11, DOX formulated in PEG-$FVE_2$ micelles exhibited a slow kinetics of release as examined in a dialysis assay. FIG. 12 illustrates that DOX formulated in PEG-$FVE_2$ micelles show superior antitumor activity over free DOX or DOXIL in an s.c. murine breast cancer model (4T1.2) ($P<0.01$ (vs. PEG-$VE_2$/DOX at 10 mg/kg); $P<0.001$ (vs. DOXIL)).

As described above, in a number of embodiments hereof, no hydrophobic segments, regions or domains are conjugated to the drug- or compound-interactive domain of the carrier agents hereof. In that regard, a drug/compound interactive domain, once identified, may be incorporated with, conjugated with or attached to a hydrophilic group. In a number of representative studies, a simple, well-defined, and easy-to-scale up carrier, $PEG_{5K}$-lysyl-(α-Fmoc-ε-t-Boc-lysine)$_2$ conjugate (PEG-$Fmoc_2$), was shown to provide high loading capacity, excellent formulation stability and low systemic toxicity for paclitaxel or PTX. In a number of representative embodiments, 9-fluorenylmethoxycarbonyl or Fmoc, as described above, was incorporated into the carrier as a functional building block to interact with drug/compound molecules. PEG-$Fmoc_2$ was synthesized via a three-step synthetic route, and it readily interacted with PTX to form mixed nanomicelles of small particle size (25-30 nm). The PTX loading capacity was about 36%. Without limitation to any mechanism, the PTX entrapment in the resultant micellar systems was believed to be achieved largely via an Fmoc/PTX π-πstacking interaction, which was demonstrated by fluorescence quenching studies and $^{13}$C-NMR. PTX formulated in PEG-$Fmoc_2$ micelles demonstrated sustained release kinetics, and in vivo distribution study via near infrared fluorescence (NIRF) imaging demonstrated an effective delivery of Cy5.5-labeled PTX to tumor sites. The maximal tolerated dose for PTX/PEG-$Fmoc_2$ (MTD>120 mg PTX/kg) was found to be higher than those for most reported PTX formulations, and in vivo therapeutic studies exhibited a significantly improved anti-tumor activity than TAXOL®, a clinically used formulation of PTX available from Bristol-Myers Squibb Company.

In a number of studies, Fmoc-containing PEG-lipid conjugates were found to be more effective than the counterparts without a lipid motif in formulating a number of hydrophobic agents. A PEG-Fmoc conjugate without a lipid motif, $PEG_{5000}$-lysyl-(α-Fmoc-ε-t-Boc-lysine)$_2$ (PEG-$Fmoc_2$), was found to be highly effective in solubilizing PTX. Moreover, PEG-$Fmoc_2$ was significantly more effective than a counterpart with a hydrophobic/lipid segment, region or domain ($PEG_{5000}$-lysyl-(α-Fmoc-ε-oleic acid-lysine)$_2$ (PEG-(Fmoc-OA)$_2$)) in formulating PTX.

Figure 13:
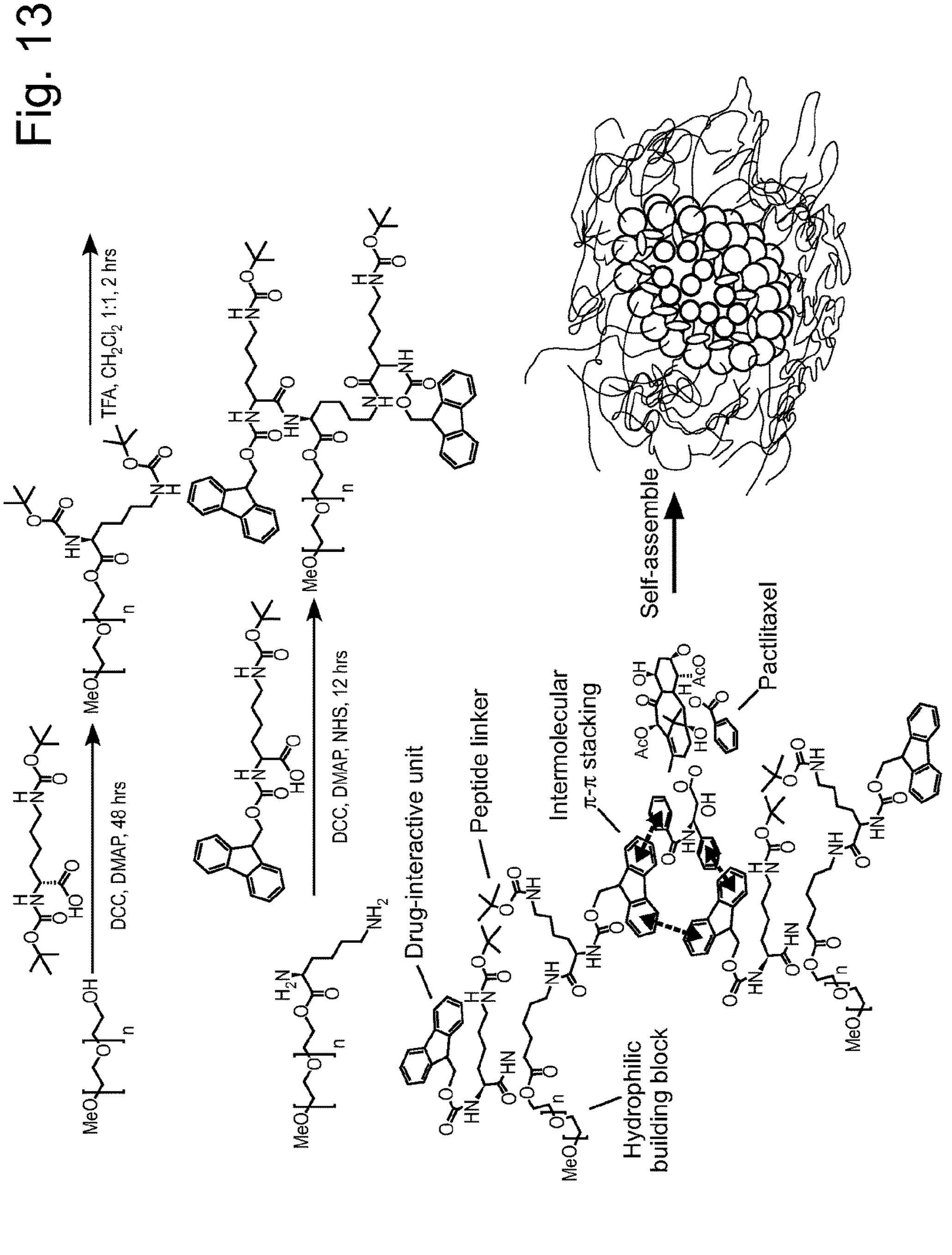
FIG. 13 illustrates a synthetic route for PEG-Fmoc and an idealized schematic representation of self-assembled PEG-Fmoc/paclitaxel or PTX based on carrier-drug intermolecular π-π stacking.

PEG-$Fmoc_2$ was readily synthesized via three steps as depicted in FIG. 13. PEG-$Fmoc_2$ readily formed small-sized (25-30 nm) micelles in aqueous solution. Negative-staining EM showed homogeneously distributed spherical particles. This is different from PEG-(Fmoc-OA)$_2$ which showed tubular morphology on EM, suggesting formation of filamentous micelles. PEG-$OA_2$ are known to form spherical micelles. Taken together, these data suggest that both Fmoc and lipid motifs contribute to the formation of unique structure of PEG-(Fmoc-OA)$_2$.

PEG-$Fmoc_2$ readily formed mixed micelles with PTX and loading of PTX had minimal effect on the size of the particles as determined by DLS. The small size and homogeneous distribution of the particles were further confirmed by negative-staining TEM. $^1$H-NMR spectrum analysis showed that the signals from both PEG-$Fmoc_2$ and PTX were clearly detected when they were mixed in $CDCl_3$. In contrast, all of the proton signals of Fmoc and PTX were greatly suppressed in deuterated water, indicating a complete encapsulation of PTX inside core area of self-assembled particles in aqueous solution. The CMC value of the PEG-Fmoc conjugate was only 5.244 μM, which is low enough to retain satisfied stability upon dramatic dilution when injected to the blood compartment.

Significantly enhanced carrier/PTX compatibility was achieved in PEG-Fmoc as compared to PEG-Fmoc-OA. As demonstrated in Table 7, stable PEG-Fmoc/PTX complexes were readily formed in aqueous solution with a PTX loading capacity up to 36% (w/w), exhibiting an impressively high capability for PTX compared to other formulations. Compared with lipid-containing surfactant PEG-Fmoc-OA, of which the maximum PTX loading capacity was reached 15% with stability for several hours in solution, PEG-Fmoc showed a dramatically improvement in both drug loading capacity and formulation stability.

TABLE 7

| | Carrier/drug molar ratio | Particle size (nm) | [a]PDI | DLC % | DLE % |
|---|---|---|---|---|---|
| PEG-Fmoc | — | 28.55 ± 0.27 | 0.488 | — | — |
| [b]PEG-Fmoc/PTX | 0.25:1 | 33.67 ± 0.60 | 0.229 | 36.16 | 61.63 |
| | 0.5:1 | 27.51 ± 0.92 | 0.264 | 22.07 | 79.43 |
| | 0.75:1 | 25.34 ± 0.63 | 0.278 | 15.88 | 84.05 |
| | 1:1 | 26.98 ± 0.20 | 0.426 | 12.41 | 81.66 |

[a]PDI, polydispersity index.
[b]PTX concentration were kept at 1 mg/mL, drug-free carrier concentration was 5 mg/mL.

The effect of freezing and lyophilization on PEG-Fmoc/PTX complexes was studied, since lyophilization is typically necessary for long-time storage in clinical practice. After lyophilization, the obtained white powder of PEG-Fmoc/PTX was readily dissolved in water to re-constitute a clear solution without any addition of cryo-protectants. No major changes in size distribution were observed following lyophilization and reconstitution.

As an important indicator of formulation stability, release kinetics of PTX from PEG-Fmoc/PTX was evaluated through dialysis method, and TAXOL was studied for comparison. PEG-Fmoc/PTX complex exhibited sustained release profile in PBS pH 7.4 at 37° C. After the first 24 h, only 19.3% of entrapped PTX was released from PEG-Fmoc/PTX, while 40.4% of PTX was released from TAXOL formulation. Even after 72 h, only 23.5% of PTX was released from PEG-Fmoc/PTX. Without limitation to any mechanism, a strong carrier-drug interaction allows the PEG-Fmoc/PTX hereof to perform as a stable formulation of PTX in physiological environment, which may contribute to a prolonged circulating duration in the blood stream, an enhanced chance to accumulate in tumors through passive targeting, and a reduced premature release of cytotoxic drugs resulting from early leakage.

To further investigate the in vivo fate of PEG-Fmoc/PTX, near infrared fluorescent (NIR) imaging was utilized to track the biodistribution of PEG-Fmoc/PTX in mice after i.v. injection. In the studies, Cy5.5 (a near infrared fluorescent probe) was conjugated to PTX, and a complex with PEG-Fmoc was formed. The complex was injected into SCID mouse bearing CL-1 human prostate cancer xenografts. Cy5.5-PTX was largely found in tumor sites 24 h after the administration without apparent accumulation in major organs, and substantial amounts of signal remained at tumor sites even 96 h later. After completion of the study after 96 h, major organs and tumors were excised, and ex vivo imaging was performed. Only mild fluorescence signal was detected in lung and kidneys, and weak signal detectable in liver and spleen, showing a reduced clearance of complexes through the reticuloendothelial system (RES). However, strong fluorescence signal of Cy5.5-PTX was recorded in tumor sites, which significantly differed from the fate of free Cy5.5-PTX solubilized by Cremophor EL/ethanol, wherein main distribution was observed in the kidneys (indicating rapid elimination). Without limitation to any mechanism, the efficient and tumor-selective accumulation of PEG-Fmoc/PTX-Cy5.5 at tumor tissue may be attributed to its small size (below 30 nm), taking full advantage of enhanced permeability and retention or EPR effect, and excellent in vivo stability contributing to a prolonged circulation and enhanced chances for passive targeting.

The maximum tolerated dose (MTD) of PEG-Fmoc/PTX was then studied in tumor-free mice for evaluation of its in vivo safety profile. TAXOL was utilized as a commercially available comparison. Five different doses of PEG-Fmoc/

PTX and three doses of TAXOL were tested in BALB/c mice through i.v. injection, followed by monitor of body weight and signs of toxicity of these animals. As shown in Table 8, TAXL was tolerable at a maximum dosage of 20 mg PTX/kg with avoidance to mice death, although several abnormal activities (such as convulsion and retarded motion) were already observed in most of mice immediately after injection. Compared with TAXOL, PEG-Fmoc/PTX exhibited an improved safety profile. Even at a dosage as high as 120 mg PTX/kg, 6-fold higher than the maximum tolerated dose of TAXOL, no mice death and significant weight loss were observed over the entire duration of test. This high MTD of PEG-Fmoc/PTX compares favorably to most reported PTX micellar formulations, and is consistent with its high formulation stability, slow release profile, and less tendency to accumulate in major organs as illustrated above (which may provide a much broader dosage window of PTX for enhanced therapeutic efficacy in clinic cancer therapy).

TABLE 8

| Formulation | Does (mg PTX/kg) | Mice death | Weight loss (%) |
|---|---|---|---|
| TAXOL | 15 | 0/4 | 0.49 |
| | 20 | 0/4 | −4.96 |
| | 25 | 1/4 | −4.35 |
| PEG-Fmoc/PTX | 30 | 0/4 | −2.77 |
| | 50 | 0/4 | −2.82 |
| | 75 | 0/4 | −5.99 |
| | 100 | 0/4 | −5.12 |
| | 120 | 0/4 | −9.49 |

Figure 14A:
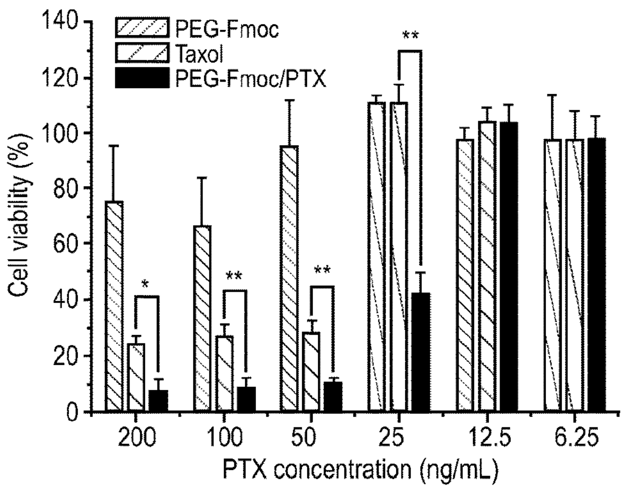
FIG. 14A illustrates in vitro tumor cell inhibition in a 4T1.2 mouse breast cancer cell line.
Figure 14B:
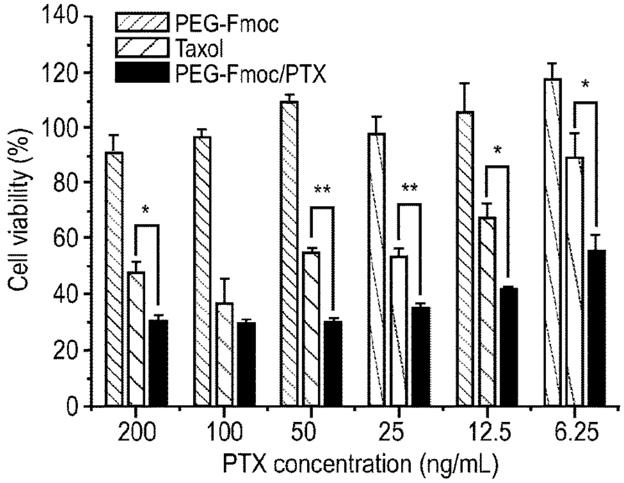
FIG. 14B illustrates in vitro tumor cell inhibition in a human prostate cancer cell line, PC-3.
Figure 14C:
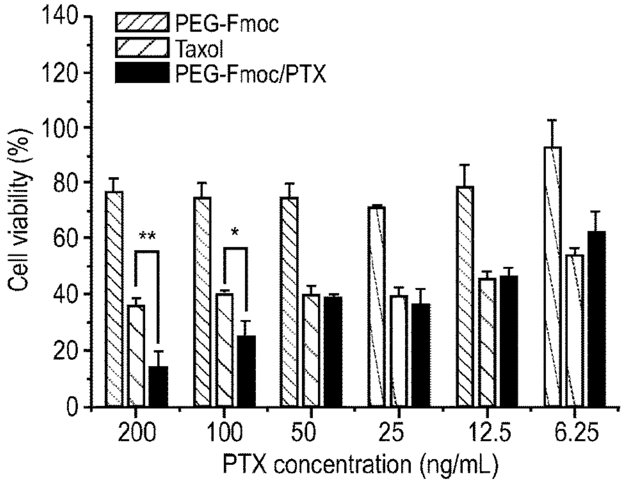
FIG. 14C illustrates in vitro tumor cell inhibition in a human prostate cancer cell line, DU145.

The tumor-inhibitory efficacy of PEG-Fmoc/PTX was also investigated both in vitro and in vivo. In vitro cytotoxicity of PEG-Fmoc/PTX was evaluated in mouse metastatic breast cancer cell line 4T1.2, and two human prostate cancer cell lines, PC-3 and DU145. As shown in FIG. 14A through 14C, in all the treated cancer cell lines, PTX-containing nanoparticles exhibited more potent cytotoxicity than TAXOL, while the carrier itself did not show apparent toxicity to cells under the tested concentrations. Without limitation to any mechanism, the increased cytotoxicity of PEG-Fmoc/PTX may, for example, be attributable to facilitated entry of PTX into tumor cells. In the studies, the cell lines were treated with PEG-Fmoc/PTX, drug-free PEG-Fmoc and TAXOL for 72 h, and tumor cell inhibition was determined by MTT assay (* $p<0.05$ or ** $p<0.01$ was determined by Student's t-test between TAXOL and PEG-Fmoc/PTX treated cells).

Figure 15A:
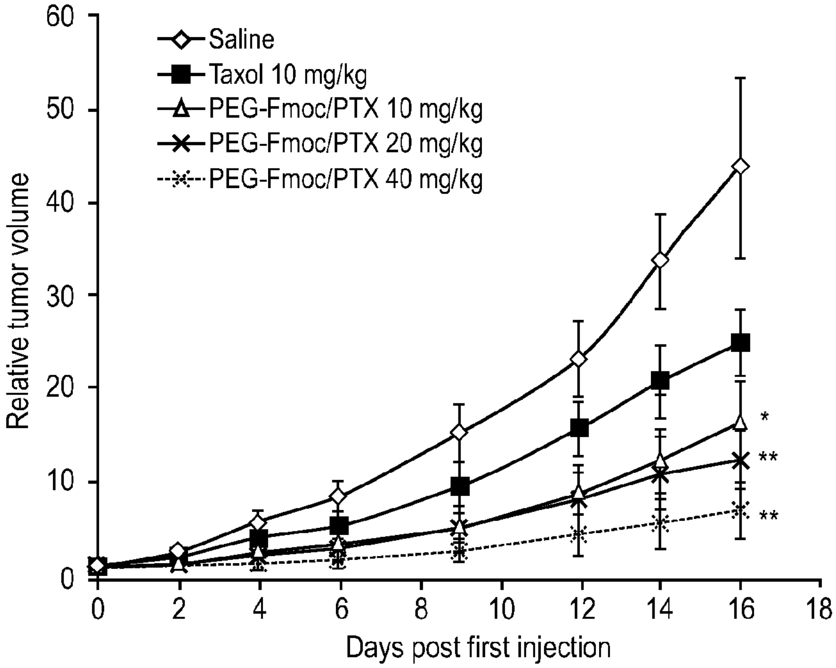
FIG. 15A illustrates an in vivo study (mice bearing 4T1.2 murine breast cancer grafts in different groups (n=5)) of the therapeutic effect of PEG-Fmoc/PTX at three dosages compared to saline and TAXOL, wherein tumor growth is plotted as relative tumor volume over time (days after initial injection).
Figure 15B:
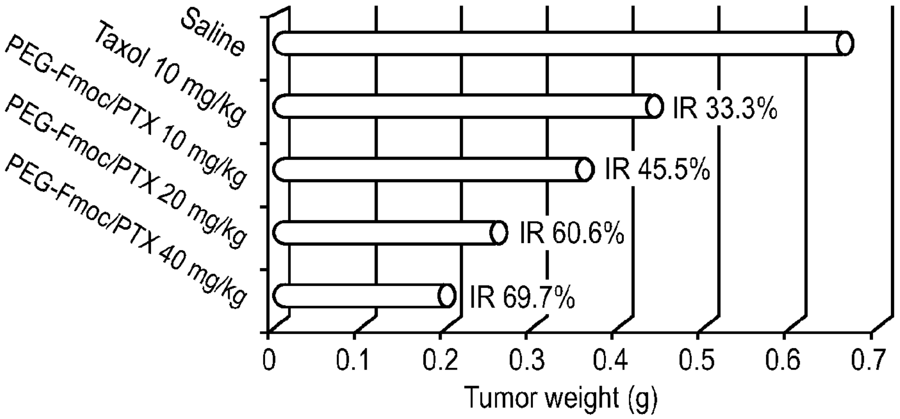
FIG. 15B illustrates an in vivo study (mice bearing 4T1.2 murine breast cancer grafts in different groups (n=5)) of the therapeutic effect of PEG-Fmoc/PTX at three dosages compared to saline and TAXOL, wherein average tumor weight (measured after excision) is set forth, and tumor growth inhibition rate (IR) was calculated using saline treated mice as a control.

The in vivo therapeutic efficacy of PEG-Fmoc/PTX was examined in mice bearing a syngeneic murine breast cancer model (4T1.2). 4T1.2 is known as a highly metastatic cancer cell line, and as demonstrated in FIG. 15A, rapid tumor growth was observed in a saline-treated mice group. Mildly retarded increase of tumor volume was obtained in TAXOL-treated mice at dosage of 10 mg PTX/kg body weight. Compared with TAXOL, PEG-Fmoc/PTX exhibited a more potent antitumor activity at the same dosage during therapy ($p<0.02$). Since a high MTD of PEG-Fmoc/PTX was demonstrated, one is provided with a higher-dosage regime than possible with TAXOL for a more efficacious therapy. Increased dosage of PTX at 20 and 40 mg/kg was thus also incorporated in this study. Further enhancement in tumor inhibition was achieved when the dose of PTX was elevated to 20 and 40 mg/kg in PEG-Fmoc/PTX ($p<0.001$), leading to a 60-70% tumor growth inhibition rate compared with saline group (FIG. 15B). It has been demonstrated that severe signs of toxicity and death occurred after a single injection of TAXOL at the dose of 20-25 mg PTX/kg. However, no mice death was observed after a sixteen-day treatment containing six consecutive injections of a high dose of PTX far beyond the maximum tolerated dose of TAXOL. No body weight loss was observed in 20 mg/kg treatment group, and a slightly decreased weight (7-8%) was noticed after consecutive injections of 40 mg/kg PTX (a two-fold higher dosage than the MTD of TAXOL) at the end of study. The significantly enhanced tumor inhibition efficacy and safety of PEG-Fmoc/PTX is clearly consistent with its biophysical properties and tumor-selective delivery.

The present systems, methods and compositions provide a mechanistically based approach for the development of compound/drug carrier agents or systems. As described above, classic lipid-based drug carrier systems rely on off-the-shelf surfactants and oils and usually involve a trial-and-error selection process for the right starting materials. The loading capacity and formulation stability are often limited for less hydrophobic drugs that do not pack well in oil cores or lipid bilayers. The present approach is fundamentally different from that of traditional lipid based formulations in several aspects. The present approach is a bottom-up approach that starts with selecting a simple structural element (motif or domain) capable of interacting with the active ingredient. This compound/drug interactive domain is then assembled with a hydrophilic domain or between a hydrophilic domain and a hydrophobic domain (for example, between one or more hydrophobic lipid chains and hydrophilic PEG brushes). In the case of amphiphilic agents hereof, the drug interactive segment is positioned at the interfacial region, which permits drugs that are, for example, not highly hydrophobic to be incorporated under less stringent hydrophobic environment.

Experimental

1. JP4-039 Studies

1(a). Materials and Methods.

α-Fmoc-ε-Boc-lysine, di-Boc-lysine, DCC, NHS, TFA, TEA were from AAPPTEC; THF anhydrous was from Acros Organic of Geel, Belgium; Monomethoxy PEG with MW of 1,000, 2,000, and 5,000, eosin Y, DMAP, ninhydrin, oleoyl chloride, sesame oil, and other unspecified reagent pure chemicals were from Sigma-Aldrich of Saint Louis, Mo. 1-palmitoyl-2-oleoyl-sn-glycero-3-phosphoethanolamine and soy phosphatidyl choline (95%) were purchased from Avanti Polar Lipids of Morrisville, N.C. JP4-039 was synthesized by Asymchem Inc. using known procedures.

1(b). Screening of Protected Amino Acid Derivatives as Solubilizers and Inhibitor of Crystallization for JP4-039.

α-acetyl-ε-Boc-lysine, α-iso-butoxycarbamoyl-ε-Boc-lysine were synthesized from α-$NH_2$-ε-Boc-lysine (1 mmole) dissolved in 5 mL of saturated sodium bicarbonate solution by adding a 4-fold excess of acetyl anhydride or isobutyl chloroformate dissolved in 5 mL of THF over a period of 5 minutes, respectively. THF was removed from the reaction mixture, the remaining mixture was diluted with 50 mL of ethyl acetate. The organic phase was washed with 20 mL of saturated $NaHCO_3$, saline, citric acid (0.5 M) and water sequentially. The organic phase was dried over anhydrous sodium sulfate, and the solvent was removed. The solid residues were recrystallized from ethyl acetate/hexanes mixture. These derivatives, together with a panel of commercially available amine protected derivatives of lysine, phenylalanine, and glycine were prepared as 1-100 mM solution or suspension in 0.1 M $Na_2HPO_4$ buffer. Meanwhile, 0.447

μg of JP4-039 dissolved in 5 μL of methanol was added to each well of a 96-well polystyrene plate. One hundred μL of amino acid solution/suspension were added to the methanol solution and mixed well. The physical status of the samples in each well was inspected visually for the physical appearance of brown crystals periodically over 2 h. Some samples were photographed under a microscope after 20 min.

1(c). Synthesis of PEG-Amino Acid or -Peptide-Lipid Conjugates.

Monomethoxy $PEG_{2,000}$-α-Fmoc-ε-Oleoyl Lysine (1): Monomethoxy $PEG_{2,000}$ OH (1 mmol) was esterified with α-Fmoc-ε-t-Boc lysine (2 mmol) with DCC (2.2 mmol) and DMAP (0.1 mmol) in $CH_2Cl_2$ at room temperature overnight. Solid precipitate was removed by filtration. The filtrate was concentrated by evaporation. The PEG derivative was precipitated with 10 volumes of cold ethyl ether and washed three times with the same solvent. Additional washes with cold ethanol were used to remove DMAP. The PEG-α-Fmoc-ε-t-Boc lysine ester was dissolved in 4 mL of $CH_2Cl_2$ to which 4 mL of TFA was added to deprotect the Boc group for 20 min at room temperature. After removal of most of $CH_2Cl_2$, the PEG-α-Fmoc-ε-$NH_2$-lysine ester was precipitated with cold ether and washed two more times with the same solvent. The PEG-α-Fmoc-ε-$NH_2$-lysine ester is end-capped with oleoyl chloride (2 mmol) and TEA (2 mmol) for 20 min. PEG-α-Fmoc-ε-Oleoyl lysine ester (1) was purified by ether precipitation for three times and ethanol precipitation twice. The yield was 87% for $PEG_{2000}$. $^1H$ NMR (400 MHz) δ 7.69-7.19 (m, 8H), 5.23-5.22 (m, 2H), 5.08 (s, 2H), 4.98-4.95 (m, 2H), 4.12-4.10 (m, 1H), 3.56-3.52 (PEG peaks), 3.26 (s, 3H), 3.21-3.17 (m, 2H), 2.09-1.88 (m, 6H), 1.27-1.16 (m, 28H), 0.77 (t, 3H).

Monomethoxy $PEG_{1000}$-α-Fmoc-lysyl-α-Fmoc-ε-(dioleoyl-lysyl) lysine (2): PEG-α-Fmoc-ε-$NH_2$-lysine ester (1 mmol) was reacted with 4 mmol of TEA, α-Fmoc-ε-t-Boc lysine (1.5 mmol), DCC (1.7 mmol) and NHS (1.5 mmol) in $CH_2Cl_2$:THF 1:1 at 0° C. for 20 minutes, then at room temperature overnight. The reaction was determined to be completed by negative results with ninhydrin tests. Monomethoxy $PEG_{1000}$ α-Fmoc-lysyl-α-Fmoc-ε-t-Boc-lysine ester was purified by cold ether and ethanol precipitations, TFA deprotection, followed by ether precipitation and washes to give $PEG_{1000}$-α-Fmoc-lysyl-α-Fmoc-ε-$NH_2$-lysine ester. This ε-$NH_2$-terminated $PEG_{1000}$-lysine derivative was end capped with 4 mmol of TEA, N,N'-dioleoyl lysine (1.5 mmol) pre-activated with DCC (1.7 mmol) and NHS (1.5 mmol) overnight. The resulting 2 was purified similarly with ether and ethanol precipitations. The yield for 2 with methoxy $PEG_{1000}$ is around 75%. $^1H$ NMR δ 7.70-7.20 (m, 24H), 5.35-5.34 (m, 2H), 5.14-5.09 (m, 6H), 4.27-4.22 (m, 2H), 3.70-3.61 (PEG peaks), 3.39 (s, 3H), 3.21-3.07 (m, 6H), 2.01-1.97 (m, 6H), 1.49-1.23 (m, 40H), 0.89 (t, 3H).

Monomethoxy $PEG_{2000}$-lysyl-(α-Fmoc-ε-oleoyl lysine)$_2$ (3): Esterification of methoxy $PEG_{2000}$-OH (1 mmol) with di-t-Boc lysine (2 mmol), DCC (2.2 mmol) and DMAP (0.1 mmol) in $CH_2Cl_2$ overnight, followed by the similar ether and ethanol precipitation steps yielded monomethoxy PEG-di-Boc-lysine ester. After TFA deprotection and ether precipitation and washes, the PEG-lysine ester was conjugated with 4 mmol of TEA, α-Fmoc-ε-t-Boc-lysine (3 mmol) with DCC (3.5 mmol) and NHS (3 mmol) in $CH_2Cl_2$:THF 1:1 at 0° C. for 20 minutes, then room temperature overnight. The reaction was confirmed to be completed by negative upon ninhydrin tests. Monomethoxy PEG-lysyl-(α-Fmoc-ε-t-Boc-lysine)$_2$ was purified by cold ether and ethanol precipitations, TFA deprotection, followed by ether precipitation and washes to give PEG-lysyl-(α-Fmoc-ε-$NH_2$-lysine)$_2$. This ε-$NH_2$-lysyl-terminated PEG derivative was end capped with 4 mmol of TEA and 4 mmol of oleoyl chloride for 20 minutes. After routine ether and ethanol precipitations and washes, purified 3 was obtained in 72% yield. $^1H$ NMR δ 7.36-7.34 (m, 16H), 5.35-5.30 (m, 4H), 5.14-5.09 (m, 4H), 4.27-4.22 (m, 6H), 3.70-3.61 (PEG peaks), 3.41 (s, 3H), 3.21-3.07 (m, 6H), 2.01-1.97 (m, 6H), 1.49-1.23 (m, 62H), 0.89 (t, 6H).

Monomethoxy $PEG_{5,000}$-lysyl-[lysyl-(α-Fmoc-ε-oleoyl lysine)$_2$]$_2$(4): The PEG-lysine ester (1 mmol) derived from methoxy $PEG_{5,000}$ was conjugated with di-t-Boc-lysine (3 mmol) with DCC (3.5 mmol) and NHS (3 mmol) in $CH_2Cl_2$: THF 1:1 at 0° C. for 20 minutes, then room temperature overnight. The reaction was confirmed to be completed by ninhydrin tests. Monomethoxy $PEG_{5,000}$-lysyl-(di-t-Boc-lysine)$_2$ was purified by cold ether and ethanol precipitations. TFA deprotection, followed by ether precipitations and washes gave PEG-lysyl-(α-$NH_2$-ε-$NH_2$-lysine)$_2$. This tetra ε-$NH_2$-terminated PEG-lysine derivative was conjugated with α-Fmoc-ε-Boc-lysine (5 mmol), DCC (6 mmol) and NHS (5 mmol) in $CH_2Cl_2$: THF 1:1 at 0° C. for 20 minutes, then room temperature overnight. The reaction was confirmed to be completed by negative upon ninhydrin tests. Monomethoxy $PEG_{5,000}$-lysyl-[lysyl-(α-Fmoc-ε-t-Boc lysine)$_2$]$_2$ was purified by cold ether and ethanol precipitations, TFA deprotection, followed by ether precipitation and washes to give PEG-lysyl-[lysyl(α-Fmoc-ε-$NH_2$-lysine)$_2$]$_2$. Finally, end capping with oleoyl chloride (8 mmol), TEA (10 mmol) for 20 minute, followed by ether and ethanol precipitations and washes gave 4 in 79% yield. $^1H$ NMR δ 7.36-7.34 (m, 32H), 5.35-5.27 (m, 8H), 5.14-5.09 (m, 7H), 4.27-4.22 (m, 6H), 3.70-3.61 (PEG peaks), 3.41 (s, 3H), 3.21-3.07 (m, 9H), 2.01-1.97 (m, 9H), 1.49-1.23 (m, 130H), 0.89 (t, 6H).

Methoxy $PEG_{2,000}$-α-Cbz-ε-oleoyl-lysine (5), $PEG_{2,000}$-α-Cbz-lysyl-α-Cbz-ε-oleoyl-lysine (6), methoxy $PEG_{2,000}$-α-Cbz-lysyl-α-Cbz-lysyl-α-Cbz-lysyl-ε-oleyol-lysine (7), and methoxy $PEG_{2,000}$-carbamoyl-1-palmitoyl-2-oleoyl-sn-glycero-3-phosphotidylethanolamine (PEG-POPE) (8). Three PEG-lysyl-lipidic conjugates with varying number of α-Cbz-lysine residues and single oleoyl chain were similarly synthesized and purified as 1 except using α-Cbz-ε-Boc-lysine, instead of α-Fmoc-ε-Boc-Lysine for 1 to 3 repeated cycles. Control surfactant $PEG_{2000}$-oleate was prepared by reacting methoxy $PEG_{2,000}$ with oleoyl chloride and TEA; and PEG-phospholipid conjugate was synthesized by reacting methoxy $PEG_{2,000}$ activated by phosgene with POPE and TEA, followed by ether precipitation.

$^1H$ NMR for lipopeptide 5: $^1H$ NMR δ 7.29-7.19 (m, 5H), 5.23-5.22 (m, 2H), 4.98-4.95 (m, 2H), 4.12-4.10 (m, 1H), 3.56-3.52 (PEG peaks), 3.26 (s, 3H), 3.21-3.17 (m, 2H), 2.09-1.88 (m, 6H), 1.27-1.16 (m, 28H), 0.77 (t, 3H).

$^1H$ NMR for lipopeptide 6: $^1H$ NMR δ 7.37-7.29 (m, 10H), 5.37-5.35 (m, 2H), 5.12-5.09 (m, 4H), 4.25-4.22 (m, 2H), 3.70-3.64 (PEG peaks), 3.40 (s, 3H), 3.21-3.17 (m, 4H), 2.03-1.89 (m, 6H), 1.40-1.24 (m, 34H), 0.90 (t, 3H).

$^1H$ NMR for lipopeptide 7: $^1H$ NMR δ 7.36-7.34 (m, 15H), 5.35-5.34 (m, 2H), 5.14-5.09 (m, 6H), 4.27-4.22 (m, 2H), 3.70-3.61 (PEG peaks), 3.39 (s, 3H), 3.21-3.07 (m, 6H), 2.01-1.97 (m, 6H), 1.49-1.23 (m, 40H), 0.89 (t, 3H).

$^1H$ NMR for PEG-POPE, compound 8: $^1H$ NMR δ 5.35-5.34 (m, 2H), 3.69-3.64 (PEG peaks), 3.92-3.96 (m, 4H), 3.57-3.55 (m, 2H), 3.39 (s, 3H), 2.29-2.28 (m, 2H), 1.37-1.27 (m, 50H), 0.89 (t, 3H).

1(d). Critical Micelle Concentration (CMC).

CMC was determined based on the red shift of the maximal absorption of Eosin Y when incorporated into more hydrophobic microenvironment in the core of micelle. Eosin Y solution was added to a final concentration of 1 mM to a series of surfactant solution prepared in distilled water and incubated for 30 minute at room temperature. $OD_{542\ nm}$ was measured and plotted against surfactant concentration from which CMC values were estimated.

1(e). Preparation of Micelle Formulations with or without JP4-039.

Typically micelles were prepared by hydration of dried thin films of amino acid derivatives or lipopeptides with suitable aqueous solutions with constant vortex, until clear solution is formed. The final concentration is approximately 100-200 mg/mL. Lipopeptides, amino acid derivatives or nitroxide compounds were first dissolved in chloroform. The solutions were aliquoted to a glass test tube, mixed well, then blown with a constant nitrogen stream to remove the bulk of the solvent. The residual solvent was removed by applying high vacuum for 2 hrs. To determine micelle-facilitated solubilization of JP4-039, various molar ratios of surfactant to drug were applied to make surfactant-drug mixture in water (final concentration of JP4-039 was 5 mg/mL). After at least 30 minutes, the samples were briefly centrifuged at 13,000 rpm. One half of the supernatants was recovered, to which an equal volume of ethanol was added to dissolve/disrupt micelle drug complexes. The amounts of drug in the samples were quantitated using $OD_{448\ nm}$.

1(f). Particle Size Measurement.

To estimate hydrodynamic sizes of micelle particles, a solution of surfactant, with or without drug incorporated, was prepared in distilled water from a dried film. Samples were further diluted ten times in distilled water and sizes were measured by laser dynamic light scattering using a particle sizer (Zetasizer Nano ZS instrument, available from Malvern Instruments Ltd of Worcestershire, United Kingdom). Size measurement of emulsion particles were conducted using a Coulter N4 particle sizer after a 100-fold dilution in saline.

1(g). Cryo-EM of Lipopeptide 4 Micelles and Lipopeptide 4-JP4-039 Complexes.

The micelles were prepared by hydration of dried lipopeptide films in distilled water at a final concentration of 100 mg/mL. The samples examined were lipopeptide 4 alone (A) and lipopeptide 4-JP4-039 complex (B) made at a molar ratio of 1.6:1. Four μL of samples, diluted 5-fold in distilled water, were immediately applied onto perforated Quantifoil grid (available from Quantifoil Micro Tools of Jena, Germany), blotted with a filter paper and plunge-frozen in liquid ethane using an FEI Vitrobot™ Mark III (available from FEI of Hillsboro, Oreg.). Low dose (10~15 $e^-/Å^2$) projection images were collected on a 4K×4K Gatan CCD camera (available from Gatan, Inc. of Warrendale, Pa.), with an FEI Tecnai TF20 electron microscope at nominal magnification of 29,000 to 50,000 and underfocus values ranging from 1.0 to 2.5 μm.

The diameters of lipopeptide 4 tubular micelles (~100 counted) and the length of bar-shaped JP4-039-lipopeptide 4 mixed micelles (~240 counted) were measured using a density plot tool in Gatan Digital Micrograph software (available from Gatan, Inc. of Warrendale, Pa.).

Cryo-electron microscopy (cryo-EM) images for selected lipopeptides confirmed the presence of self-assembled structures with long tubular shape at 20 mg/mL of 3 (not shown) and 4 (FIGS. 3A and 3B). The tubular structures have an electron-light center region of 2.8-4.0 nm in thickness (3.5±0.4 nm, n=22), presumably the micelle core that is made of lipid chains. The light core is surrounded by an electron-dense peripheral wall, presumably the Fmoc-lysine-containing interface region. The average diameter of the tubular structure, measured from the distance between the mid-points of the dense walls, is ~5.6±0.4 nm. The thickness of electron-dense regions is ~⅓ to ½ of the thickness of the electron-light center region. The PEG chains are not electron-dense enough to be revealed with cryo-EM. The reported lipid-anchored $PEG_{5,000}$-PE conjugates displayed on the surface of liposomes is 10-15 nm in thickness. Assuming that this parameter applies to these tubular-shaped PEG-lipopeptide micelles, the overall diameter including the PEG layer would be in the 27-40 nm range.

The JP4-039 loaded micelles showed significantly reduced viscosity. The particle sizes measured with laser dynamic light scattering method were also smaller for JP4-039 loaded PEG-lipopeptide 4 than the empty micelles (Table 4). When JP4-039 was present, cryo-EM images showed a mixture of many small dots (~90%, n=388, FIG. 3B) and truncated bar-like structures (~10%). The diameters for the dots and bars were slightly less than that of the tubular micelles observed in the sample of lipopeptide alone. The bar structures were variable in length, ranging from ~30 to 300 nm, with a median length under 60 nm. The size distribution of the JP4-039-loaded micelles on cryo-EM agrees with the results obtained by laser dynamic light scattering. There was no sign of crystals of the free drug (see FIG. 3B).

1(h). Fluorescence Quenching Studies.

Micelle formulations with or without JP4-039 were prepared with 10 mg of lipopeptide 4 containing 0, 0.25 or 0.5 mg of JP4-039 by hydration method in 300 μl of saline. The fluorescence intensity was recorded on a Synergy H1 Hybrid reader (available from BioTek of Winooski, Vt.), using an excitation wave length of 300 nm and varied emission wave length from 350 nm to 500 nm.

1(i). $^1H$ NMR Spectroscopies for Micelle Formulations.

Micelles were prepared from lipopeptide 4 or α-Fmoc-ε-tBoc-lysine (with or without JP4-039 or 4-acetamide-TEMPO) in $D_2O$ containing 100 mM NaCl (for lipopeptide 4) or 100 mM $KHCO_3$ (for α-Fmoc-ε-Boc-lysine). $^1H$ NMR spectrum was recorded using a Bruker 400 MHz NMR (available from Bruker Corporation of Billerica, Mass.) and a recycling pulse delay of 20 s was used to ensure the accurate proton integration. For initial trials, d-DMSO was used as the alternative solvent.

1(j). Hemolysis Assay.

Rat red blood cells (RBCs) were isolated from freshly collected rat blood with added anticoagulant by washing three times with 10 volumes of cold PBS (1500 rpm for 10 min) RBCs were then diluted to 2% w/v with ice cold DPBS and utilized immediately for the hemolysis assay. One mL of diluted RBC suspension was treated with various concentrations (0-5 mM) of PEG-lipopeptides, Tween 80, and Triton X-100, respectively, and then incubated at 37° C. in an incubator shaker for 2 h. The samples were centrifuged at 1500 rpm for 10 min at 4° C., and 100 μL of supernatant from each sample was transferred into a 96-well plate. The release of hemoglobin was determined by the absorbance at 540 nm using a micro-plate reader. RBCs treated with Triton X-100 and DPBS were considered as the positive and negative controls, respectively. Hemoglobin release was calculated as $(OD_{sample}-OD_{negative\ control})/(OD_{positive\ control}-OD_{negative\ control})\times100\%$.

1(k). Emulsion Formulation for JP4-039 and Stability.

JP4-039 (4 mg) were formulated in an emulsion composed of sesame oil (100 mg) and soy phosphatidyl choline (50 mg); or sesame oil (100 mg/mL), soy phosphatidyl choline (40 mg), together with a co-surfactant of either $PEG_{2,000}$-oleate (29.6 mg/mL, 0.0128 μmole), $PEG_{2,000}$-α-CBz-ε-oleoyl-lysine (32.5 mg/mL, 0.0128 μmole), $PEG_{2,000}$-α-CBz-α-CBz-ε-oleoyl-lysine (35.9 mg/mL, 0.0128 μmole), or $PEG_{2,000}$-α-CBz-lysyl-α-CBz-lysyl-α-CBz-ε-oleoyl-lysine (39.3 mg/mL, 0.0128 μmole). All ingredients were dissolved in chloroform, mixed well, and then the solvent was removed under $N_2$ stream, followed by vacuum desiccation for 2 hrs. The oily residues were suspended in saline, sonicated under an ice bath with a probe sonicator with a maximal output of 20 mW for 60 minutes under a $N_2$ stream, until the sizes were reduced below 150~250 nm. Initial particle sizes were estimated by laser dynamic light scattering method (Coulter N4 particle sizer). Drug loading rate in the freshly prepared formulations and those stored at 4° C. for 7 days were determined after low speed centrifuge to remove any precipitates in the samples. Organic components were extracted three times with equal volume of chloroform under vortex. The organic phase was pooled and the solvent were removed under a nitrogen stream. The residues were reconstituted to 1 ml with chloroform. The drug contents were determined using $OD_{448\ nm}$ reading.

1(l). Radiation Mitigation Activity Against Whole Body Irradiation in Mice.

All mice were irradiated with a total-body dose of 9.5 Gy delivered by a $^{137}$Cs J. L. Shepherd Mark 1 irradiator (available from J.L. Shepherd & Associates of San Fernando, Calif.) at a dose rate of 0.8 Gy/min. The mice were then divided into two groups (10-15 mice per group). These mice were injected i.p. with JP4-039 formulated in emulsion or control formulations alone 24 h after irradiation. The JP4-039 dosage was 20 mg/kg. Mice were followed until they have lost 20% of their body weight or appear moribund, at which time they are euthanized.

2. Paclitaxel Studies

2(a). PTX Formulated in Amphiphilic Agents

2(a)(i). Materials:

Paclitaxel (98%) was purchased from AK Scientific Inc. (Union City, Calif.). Succinate anhydride, tris(hydroxymethyl)aminomethane (tris), 9-fluorenylmethoxycarbonyl chloride (Fmoc-Cl), p-Toluenesulfonic acid (TsOH) and Fmoc-Lys(Boc)-OH were all purchased from Sigma-Aldrich (Saint Louis, Mo.). N-hydroxysuccinimide (NHS) and Dicyclohexylcarbodiimide (DCC) were purchased from Alfa Aesar (Ward Hill, Mass.). 4-(dimethylamino) pyridine (DMAP) was purchased from Calbiochem-Novabiochem Corporation (San Diego, Calif.). FTS was synthesized and purified according to published literature.

2(a)(ii). Synthesis of $PEG_{5K}$-$FTS_2$ and $PEG_{5K}$-Fmoc-$FTS_2$:

$PEG_{5K}$-Fmoc-$FTS_2$ was synthesized via solution condensation reactions from MeO-PEG-OH with a molecular weight of 5000 Da. Succinate anhydride (5 eq) was coupled onto the O terminal of PEG using DMAP (5 eq) in dichloromethane ($CH_2Cl_2$) for overnight. PEGylated molecules were precipitated by adding cold ether and washed with ether twice. Tris was coupled by using NHS (3 eq) and DCC (3 eq) as coupling reagents in $CH_2Cl_2$ for one day. The PEGylated molecules were precipitated by adding cold ether and washed with ether twice. Acetonide was using TsOH as a catalyst in acetone. Fmoc group was coupled with OH using Fmoc-Cl (2 eq) and $NEt_3$ (3 eq) in $CH_2Cl_2$ overnight. PEGylated molecules were precipitated by adding cold ether and washed with ether twice. Acetonide groups was removed by the treatment with 1% TsOH in $CH_2Cl_2$. FTS (4 eq) were coupled using DCC (4 eq) and DMAP (0.4 eq) as coupling reagents. PEGylated molecules were precipitated by adding cold ether and washed with ether twice. This molecule was lyophilized to yield a white powder.

2(a)(iii). Preparation and Characterization of PTX-Loaded Micelles:

PTX (10 mM in chloroform) and $PEG_{5K}$-Fmoc-$FTS_2$ conjugate (10 mM in chloroform) were mixed with various carrier/drug ratios. The organic solvent was removed by nitrogen flow to form a thin film of drug/carrier mixture. The film was dried under vacuum for 1 h to remove the remaining solvent. DPBS was added to hydrate the thin film and the drug-loaded micelles were formed. Unincorporated PTX (precipitate) was removed by filtering with a syringe filter (pore size: 220 μm). The drug-free and PTX-solubilized $PEG_{5K}$-$FTS_2$ micelles were similarly prepared as described above.

The particle size of micelles was measured by a Zetasizer (DLS) (Zetasizer Nano ZS instrument, Malvern, Worcestershire, United Kingdom). The micelle concentrations were kept at 1 mg/mL.

The drug loading efficiency was quantified by high performance liquid chromatography (HPLC) (Alliance 2695-2998 system). The reverse phase LICHROSPHER® 100 RP-18 (5 μm) column was used and the mobile phase consisted of methanol/water (80:20 v/v). LICHROSPHER is a chromatographic absorbent available from Merck Milipore of Darmstad, Germany PTX-loaded micelles were diluted with MeOH (micelle solution/MeOH=1/9, v/v) to dissociate drug loaded micelles. The flow rate was set at 0.8 mL/min and the column effluent was detected at 227 nm with a UV/vis detector. Drug loading capacity (DLC) and drug loading efficiency (DLE) were calculated according to the following equation:

DLC (%)=[weight of drug used/(weight of polymer+drug used)]×100%

DLE (%)=(weight of loaded drug/weight of input drug)×100%

We followed the size change of free drug and PTX-loaded micelles. The stability indicated that there was no noticeable size change during the follow-up period.

2(b). PTX Formulated in Hydrophilic Agents

2(b)(i). Materials.

Paclitaxel (PTX, 98%) was purchased from AK Scientific Inc. (Union City, Calif.). α-Fmoc-ε-Boc-lysine, di-Boc-lysine, N,N'-dicyclohexylcarbodiimide (DCC), N-hydroxysuccinimide (NHS), trifluoroacetic acid (TFA), and triethylamine (TEA) were obtained from Acros Organic (Geel, Belgium and New Jersey, USA). Monomethoxy $PEG_{5000}$, 4-dimethylaminopyridine (DMAP), ninhydrin, and other unspecified chemicals were all purchased from Sigma-Aldrich (Saint Louis, N.J.). Dulbecco's phosphate buffered saline (DPBS), Dulbecco's Modified Eagle's Medium (DMEM), fetal bovine serum (FBS), 100× penicillin-streptomycin solution were all purchased from Invitrogen (of Grand Island, New Your). All solvents used in the studies were HPLC grade.

2(b)(ii). Cell Culture.

4T1-2 is a mouse metastatic breast cancer cell line. PC-3 and DU145 are two androgen-independent human prostate cancer cell lines. They were all cultured at 37° C. in DMEM containing 10% FBS and 1% penicillin-streptomycin in a humidified environment with 5% $CO_2$.

2(b)(iii). Synthesis of $PEG_{5K}$-lysyl-(α-Fmoc-ε-t-Boc-lysine)$_2$ (PEG-$Fmoc_2$).

PEG-$Fmoc_2$ was synthesized largely following our published method. Briefly, 1 equiv. of monomethoxy $PEG_{5000}$ was mixed with excess amount of di-Boc-lysine and DCC in dichloromethane (DCM) with addition of DMAP, and the reaction was allowed at room temperature for 48 h. The mixture was filtered and precipitated in ice-cold ether, followed by washes with cold ethanol and ether to obtain purified $PEG_{5000}$-di-Boc-lysine. The PEG derivative was then treated with DCM/TFA (1:1, v/v) for 2 h at room temperature, followed by removal of the solvent, precipitation in cold ether, and washes with cold ethanol and ether. Finally, the deprotected $PEG_{5000}$-lysine-$NH_2$ was mixed with excess amount of α-Fmoc-ε-Boc-lysine that was preactivated with NHS, DCC, and small amount of DMAP in DCM at 37° C. for 4 h. The reaction was allowed at 37° C. till the ninhydrin test became negative, indicating the absence of free amino groups. The reaction mixture was filtered and precipitated by ice-cold ether, followed by washes with cold ethanol and ether. The obtained material was dissolved in water and filtered through a 220 nm filter, followed by lyophilization to yield the powder of purified $PEG_{5K}$-lysyl-(α-Fmoc-ε-t-Boc-lysine)$_2$.

2(b)(iv). Preparation and Biophysical Characterization of PTX/PEG-$Fmoc_2$ Mixed Micelles.

Thin-film hydration method was utilized for preparation of PTX/PEG-$Fmoc_2$ mixed nanomicelles. PEG-$Fmoc_2$ and PTX in chloroform were well mixed in a glass tube at designated molar ratios. A thin film of carrier/drug mixture was generated through removal of the organic solvent by a gentle stream of nitrogen. The trace amount of solvent was further removed via vacuum for 2 h. Then the film was hydrated and suspended in DPBS by vortex to obtain a clear solution of PTX/PEG-$Fmoc_2$ mixed nanomicelles. Any non-entrapped drug was removed by filtration through 220 nm PVDF syringe filter.

The size distribution of PTX/PEG-$Fmoc_2$ mixed nanomicelles was examined by dynamic light scattering (DLS) via a Malvern Zeta Nanosizer, and the morphology was observed by transmission electron microscopy (TEM) after negative staining. The CMC measurement was performed as reported before with pyrene as a fluorescence probe. To quantify PTX in the micelles, PTX was extracted by methanol, and detected by Waters Alliance 2695-2998 high-performance liquid chromatography (HPLC) system with a RP-18 column (250 mm×4.6 mm) equipped with a UV detector at 227 nm at room temperature. A mixture of methanol/water (80:20, v/v) was used as mobile phase at a flow rate at 0.8 mL/min. The drug loading capacity (DLC) and efficiency (DLE) were calculated as set forth above.

2(b)(v). Effect of Lyophilization/Reconstitution on Particle Sizes.

One mL of PTX/PEG-$Fmoc_2$ in DPBS was prepared as described above and the PTX concentration was kept at 1 mg/mL. The clear solution was frozen and lyophilized overnight to obtain white powder. The powder was then reconstituted with 1 mL of distilled water to obtain a clear solution. Particle sizes of the PTX-loaded micelles before and after lyophilization/reconstitution were recorded via DLS using a Zetasizer.

2(b)(vi). Fluorescence Quenching.

PTX/PEG-$Fmoc_2$ mixed micelles of various drug/carrier molar ratios were prepared in DPBS as described above, and Chol/PEG-$Fmoc_2$ and TAXOL were utilized as controls. In all the groups, the concentration of PEG-$Fmoc_2$ was fixed at 0.44 μM for comparison. The samples were placed into a 96-well plate, and examined for the fluorescence intensity at the excitation wavelength of 270 nm and emission wavelength of 300-460 nm using a Synergy H1 Hybrid Multi-Mode Microplate Reader.

2(b)(vii). In Vitro Drug Release Kinetics.

Two mL of PTX/PEG-$Fmoc_2$ mixed micelles in DPBS (PH=7.4) (1 mg PTX/mL) was prepared and placed into a dialysis bag (MWCO 12 kDa, Spectrum Laboratories) that was incubated in a tank containing 200 mL of DPBS with 0.5% (w/v) Tween 80 under gentle shaking at 37° C. At scheduled time points (0, 1, 2, 4, 8, 24, 48, and 72 h), the concentration of PTX remaining in the dialysis bag was measured by HPLC as described above. TAXOL formulation (6 mg PTX/mL in Cremophor EL/ethanol, 1:1, v/v) was diluted with DPBS to a final PTX concentration of 1 mg/mL and utilized as a control.

2(b)(viii). In Vitro Cytotoxicity.

Mouse metastatic breast cancer cell line 4T1.2, and two human prostate cancer cell lines PC-3 and DU145 were utilized to evaluate the in vitro cytotoxicity of PTX/PEG-$Fmoc_2$. Cells were seeded in 96-well plates at 1000 (4T1.2), 2000 (DU145) and 3000 (PC-3) cells per well. Twenty-four h later, cells were treated with PTX/PEG-$Fmoc_2$ or TAXOL with PTX concentrations ranging from 6.25 to 200 ng/mL. Seventy-two h later, 20 μL of 3-(4,5-dimethylthiazol-2-yl)-2,5-diphenyltetrazoliumbromide (MTT, 5 mg/mL) was added into each well. Following incubation for 4 h, the medium was removed and 150 μL of DMSO was added to each well to solubilize the formazan crystal. The absorbance of each well was detected at 550 nm with a reference wavelength at 630 nm using a microplate reader, and cell viability was calculated based on the formula below. Untreated cells were included as a control.

$$\% \text{ cytotoxicity}=[1-(OD_{treat}-OD_{blank})/(OD_{control}-OD_{blank})]\times 100\%$$

2(b)(ix). Animals.

Female BALB/c mice (6 to 8 weeks) were purchased from Charles River (Davis, Calif.), and were housed under pathogen-free conditions according to AAALAC guidelines. All animal-related experiments were performed in full compliance with institutional guidelines and approved by the Animal Use and Care Administrative Advisory Committee at the University of Pittsburgh.

2(b)(x). Maximum Tolerated Dose (MTD) Study.

BALB/c mice were randomly divided into seven groups (n=4) and i.v. administered with PTX/PEG-$Fmoc_2$ (30, 50, 75, 100, and 120 mg PTX/kg) or TAXOL (15, 20, and 25 mg PTX/kg). Mice were then followed for 10 days for survival and changes in body weight. The MTD was determined at a dose of PTX that leads to neither animal death nor significant changes in the general appearance or greater than 15% of body weight loss over the entire experimental period.

2(b)(xi). Fluorescence Optical Imaging.

Near infrared fluorescence (NIRF) imaging was performed to investigate the in vivo biodistribution of PTX/PEG-$Fmoc_2$ mixed nanomicelles using PTX labeled with Cy5.5, a near infrared fluorescence dye. Two hundred μL of PTX-Cy5.5/PEG-$Fmoc_2$ mixed nanomicelles (0.4 PTX-Cy5.5 mg/mL) were i.v. injected into SCID mice bearing CL1 xenograft. At scheduled times, mice were anesthetized and scanned with a Carestream Molecular Imaging's In-Vivo Imaging FX Pro, using a 30 s exposure time with the excitation at 630 nm and the emission at 700 nm. At the end of the imaging study, all the mice were sacrificed and the major organs and tumors were excised for ex vivo imaging.

2(b)(xii). In Vivo Therapeutic Efficacy.

A syngeneic mouse breast cancer model (4T1.2) was established via s.c. inoculation of $2\times10^5$ of 4T1.2 cells into the right flank of female BALB/c mice, and the treatments were initiated when the tumor size reached ~50 $mm^3$. Mice were divided randomly into five groups (n=5) and received i.v. injection of saline, TAXOL (10 mg PTX/kg), and PTX/PEG-Fmoc$_2$ (10, 20, and 40 mg PTX/kg), respectively. Tumor volumes were measured by a caliper and calculated based on the formula: $(L\times W^2)/2$, where L is the longest and W is the shortest tumor diameters (mm). The data were presented as relative tumor volume (RTV, the tumor volume at a given time point divided by the tumor volume prior to first treatment). Mice were sacrificed when tumors developed ulceration. Changes in body weights of all mice were also monitored during the entire course of treatment to evaluate the potential toxicity of the formulations. Tumors were harvested at the completion of the experiment and tumor weights were measured. Tumor growth inhibition rate (IR) was calculated as: 1−(mean tumor weight of PTX treated group/mean tumor weight of saline treated group)*100%.

2(b)(xii). Statistical Analysis.

Statistical analysis was performed with two-tailed Student's t-test between two groups, and $p<0.05$ was considered statistically significant. One-way ANOVA was conducted to assess significance among multiple groups, followed by two-tailed Student's t-test if $p<0.05$.

3. Doxorubicin Studies

3(a). Materials

Doxorubicin or DOX (>99%) for studies with Fmoc-FTS systems was purchased from LC Laboratories (of Woburn, Mass.). L-α-phosphatidylcholine (Soy PC), ammonium sulfate ($(NH_4)_2SO_4$) and DSPE-PEG(2000)-$OCH_3$ were purchased from Avanti® Polar Lipids, Inc (of Alabaster, Ala.). Cholesterol (Chol) was purchased from Sigma-Aldrich (of Saint Louis, Mo.).

Liposome was prepared by thin lipid film hydration followed by probe sonication. Unmodified liposomes were composed of SPC:Chol:DSPE-PEG2000 in a 7:3:0.5 molar ratio. A chloroform solution of the lipid components was mixed and evaporated under a gentle stream of $N_2$ followed by vacuum for at least 4 hours. The dried lipid films were hydrated with ammonium sulfate (123 mM) at 4° C. overnight. After a brief vortex, the suspension was then probe sonicated for 1 hour at a power of 3 watts. Liposomes containing ammonium sulfate were passed through a column pre-equilibrated with saline. Liposome suspensions were then mixed with a DOX saline solution. The final Liposome/DOX was generated using gel chromatography to remove unencapsulated DOX. DOX saline solution was stirred with triethylamine (2 eq) in a mixture of chloroform ($CHCl_3$)/methanol (MeOH) (1:1, v/v) to remove HCl from DOX.HCl. The drug-free and DOX-solubilized micelles were similarly prepared as PTX-loaded micelles.

DOX for studies with Vitamin E and Fmoc was purchased from AK Scientific Inc (of Union City, Calif.). Methoxy-PEG$_{5,000}$-OH, succinate anhydride, Boc-lys-(Boc)-OH and Fmoc-lys-(Boc)-OH were all purchased from Sigma-Aldrich (Saint Louis, Mo.). D-alpha-tocopheryl (Vitamin E) was purchased from Tokyo Chemical Industry (of Portland, Oreg.). DCC was purchased from Alfa Aesar (MA, USA). DMAP was purchased from Calbiochem-Novabiochem Corporation (of San Diego, Calif.). All solvents used in this study were HPLC grade.

3(b). In Vivo Tumor Therapy Study for DOX-Loaded PEG$_{5K}$-Fmoc-FTS$_2$:

A syngeneic murine breast cancer model (4T1.2) was used to examine the therapeutic effect of different formulations of DOX. $1\times10^5$ 4 T1.2 cells in 200 μL PBS were inoculated s.c. at the right flank of female BALB/c mice. Treatments were started when tumors in the mice reached a tumor volume of ~50 mm$^3$ and this day was designated as day 1. On day 1, these mice were randomly divided into eight groups (n=5) and administered i.v. with PBS (control), DOX (5 mg DOX/kg), Liposome/DOX (5 mg DOX/kg), DOX-loaded PEG$_{5K}$-Fmoc-FTS$_2$ micelles (5, 10 mg DOX/kg), and DOX-loaded PEG$_{5K}$-FTS$_2$ (5 mg DOX/kg), respectively on days 1, 4, and 7. Tumor sizes were measured with digital caliper three times a week and calculated by the formula: $(L\times W^2)/2$, where L is the longest, W is the shortest in tumor diameters (mm). To compare between groups, relative tumor volume (RTV) was calculated at each measurement time point (where RTV equals to the tumor volume at a given time point divided by the tumor volume prior to first treatment). Mice were sacrificed when tumor reached 2000 mm$^3$. The body weights of all mice from different groups were measured every three days.

3(c). Synthesis of PEG$_{5K}$-VE$_2$ (PEG-VE$_2$).

Initially, (Boc)lysine(Boc)-OH (4 eq.) was coupled onto the terminal —OH of PEG$_{5K}$ using DCC (4 eq.) and DMAP (0.1 eq.) as coupling reagents in DCM for overnight. PEG-Lys-DiBoc ester was precipitated and washed three times with cold ethanol and ether, respectively. Then Boc groups were removed by the treatment with 50% trifluoroacetic acid in DCM. The resultant (PEG$_{5K}$-Lysine ester) was precipitated and washed three times with cold ethanol and ether, respectively. Then Vitamin E succinate (6 eq.) was coupled to the amino groups of lysine, yielding PEG$_{5K}$-VE$_2$. The final product was further precipitated and washed three times with cold ethanol and ether, respectively. The final product was lyophilized to yield white powder. The synthesis route is set forth in FIG. 10A.

3(d). Synthesis of PEG$_{5K}$-Fmoc-VE$_2$ (PEG-FVE$_2$):

PEG-FVE$_2$ was synthesized via solution phase condensation reactions from MeO-PEG-OH with a molecular weight of 5,000 Da. Fmoc-lys-(Boc)-OH (4 eq.) was coupled onto the terminal —OH of PEG using DCC (4 eq.) and DMAP (0.2 eq.) as coupling reagents in DCM for overnight. Fmoc-lys-(Boc) PEG ester was precipitated and washed three times with cold ethanol and ether, respectively. Then, Boc groups were removed by the treatment with 50% trifluoroacetic acid in DCM, and the Fmoc-lysyl PEG ester was precipitated and washed three times with cold ethanol and ether, respectively. Boc-lys-(Boc)-OH (2 eq.) was coupled onto the terminal-NH2 of Fmoc-lysyl PEG ester using DCC (2 eq.) and DMAP (0.1 eq.) as coupling reagents in DCM for overnight. The di-Boc PEG ester was precipitated and washed three times with cold ethanol and ether, respectively. Then, Boc groups were removed by the treatment with 50% trifluoroacetic acid in DCM, and the di-NH2 PEG ester was precipitated and washed three times with cold ethanol and ether, respectively. The resulting white powder precipitate was dried under vacuum. Vitamin E succinate (4 eq.) was coupled to the deprotected amino groups of lysine with the assistance of DCC (4 eq.) and DMAP (0.2 eq.). The resulting PEG-FVE$_2$ was precipitated and washed three times with cold ethanol and ether, respectively. The final product was subsequently dialyzed against water and lyophilized to yield white powder. The synthetic route is set forth in FIG. 10B.

3(e). Preparation of Physiochemical Characterization of DOX-Loaded PEG-VE$_2$ and PEG-FVE$_2$ Micelles:

First DOX HCl was neutralized by 3 molar equivalent of triethylamine in $CHCl_3$/MeOH (1:1. v:v) to remove HCl from parent compound. DOX (10 mM in $CHCl_3$/MeOH) was added to PEG-FVE$_2$ (10 mM in chloroform) with different carrier/drug molar ratios. The organic solvent was first removed by nitrogen flow to form a thin dry film of drug/carrier mixture. The dry film was further dried under high vacuum for 2 h to remove any traces of remaining solvent. The film of mixture was then reconstituted in saline without further sonication. DOX-Loaded PEG-$VE_2$ was prepared similarly. The mean diameter of drug-formulated micelles was evaluated by dynamic light scattering (DLS). The concentration of DOX loaded in micelles was examined by HPLC with the detector set at 227 nm. The drug loading capacity (DLC) and drug loading efficiency (DLE) were calculated as set forth above.

3(f). In Vitro Release Kinetics.

The in vitro release kinetics of DOX was carried out by dialysis technique by employing DPBS (PH=7.4) containing 0.5% (w/v) Tween 80 as the release medium. Free DOX was employed as a control. Two mL of DOX-loaded PEG-$VE_2$ or PEG_$FVE_2$ nanoformulations (1 mg DOX/mL) were sealed in dialysis tubes (MWCO=12 KDa, Spectrum Laboratories). The dialysis tubes were immersed in 500 mL release medium in a beaker covered with parafilm. The beakers were kept in an incubator shaker at 100 rpm and 37° C. At different time points, the concentration of DOX retained in the dialysis tubes was measured by HPLC with the detector set at 227 nm. Values were reported as the means from triplicate samples.

3(g). In Vivo Antitumor Therapeutic Investigation:

A syngeneic murine breast cancer model (4T1.2) was used to evaluate the therapeutic efficacy of different DOX formulations. Briefly, $2\times10^5$ 4 T1.2 cells in 200 L saline were inoculated subcutaneously at the right flank of female BALB/c mice. When tumors in the mice reached a volume around 50-100 $mm^3$, mice were randomly assigned to five groups of 5 mice each and this day was designated as day 1. From day 1, mice were intravenously administered three times by free DOX (10 mg/kg), DOXIL (10 mg/kg), DOX-loaded PEG-$VE_2$ (10 mg/kg) and DOX-loaded PEG-$FVE_2$ (10 and 20 mg/kg) at a 3 days interval on days 1, 4, 7, respectively. Tumor sizes were measured with digital caliper on days 1, 4, 7, 10, 12, 15, 18, 21, 25 and calculated according to the following formula: $(L\times W^2)/2$, where L and W are the length and width of each tumor, respectively. To better compare between groups, relative tumor volume (RTV) was calculated at each measurement time point (where RTV=the tumor volume at a given time point/the tumor volume prior to first treatment). Mice were sacrificed when tumor reached 2000 $mm^3$ or developed severe ulceration, whichever comes first, and the tumors were weighed.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method of creating a formulation for a compound, comprising:

creating a carrier agent by conjugating at least one compound interactive domain comprising at least one fluorenylmethyloxycarbonyl group or a derivative thereof with at least one hydrophilic domain and with at least one hydrophobic domain so that the at least one compound interactive domain is positioned between the at least one hydrophilic domain and the at least one hydrophobic domain, the compound interactive domain being different from the at least one hydrophilic domain and from the at least one hydrophobic domain, and combining the compound and the carrier agent to create the formulation.

2. The method of claim 1 wherein the at least one hydrophobic domain comprises a lipid.

3. The method of claim 1 wherein the at least one hydrophilic domain comprises at least one hydrophilic oligomer or at least one hydrophilic polymer.

4. The method of claim 3 wherein the hydrophilic oligomer or the hydrophilic polymer is a polyalkylene oxide, a polyvinylalcohol, a polyacrylic acid, a polyacrylamide, a polyoxazoline, or a polypeptide.

5. The method of claim 1 wherein the at least one hydrophilic domain comprises at least one ionic group, at least one carboxylic acid group, at least one amine group, at least one saccharide group, or at least one polysaccharide group.

6. The method of claim 1 wherein the formulation forms a complex selected from a group consisting of a micelle, an emulsion, a cream, a liposome, a spherulite, a solid-lipid nanoparticle, a hydrogel or a cubic phase lipogel.

7. The method of claim 1 wherein the at least one hydrophobic domain comprises at least one lipid, at least one tocopherol, at least one hydrophobic oligomer or at least one hydrophobic polymer.

8. The method of claim 1 wherein the at least one hydrophobic domain comprises at least one of a polymethylacryl, a polyethylene, a polystyrene, a polyisobutane, a polyester, a polypeptide, or a derivative thereof.

9. The method of claim 1 wherein the at least one hydrophobic domain comprises a farnesylthiosalicylate group.

10. The method of claim 1 wherein the compound is JP4-039, paclitaxel, FK506, cyclosporin A, a protoporphyrin, GW4064, rose bengal, epigallocatechin gallate, curcumin, indomethacin, tamoxifen or doxorubicin.

11. The method of claim 1 wherein the compound is paclitaxel and the hydrophilic domain comprises polyethylene glycol.

12. The method of claim 1 wherein the at least one compound interactive domain of the carrier is covalently bonded to the at least one hydrophilic domain.

13. The method of claim 1 wherein the at least one compound interactive domain of carrier agent is covalently bonded to the at least one hydrophilic domain and is covalently bonded to the at least one hydrophobic domain.

14. A formulation to deliver a compound to a patient, comprising:

the compound and a carrier agent comprising at least one hydrophilic domain conjugated with at least one compound interactive domain comprising at least one fluorenylmethyloxycarbonyl group or a derivative thereof, and at least one hydrophobic domain, conjugated with the at least one compound interactive domain, wherein the at least one compound interactive domain is positioned between the at least one hydrophilic domain and the at least one hydrophobic domain.

15. The formulation of claim 14 wherein the at least one hydrophobic domain comprises at least one lipid, at least one tocopherol, at least one hydrophobic oligomer or at least one hydrophobic polymer.

16. A method of creating a formulation to deliver a compound to a patient, comprising:

providing a carrier agent comprising at least one hydrophilic domain conjugated with at least one compound interactive domain comprising at least one fluorenylmethyloxycarbonyl group or a derivative thereof and at least one hydrophobic domain conjugated with the at least one compound interactive domain, wherein the at least one compound interactive domain is positioned between the at least one hydrophilic domain and the at least one hydrophobic domain, the compound interactive domain being different from the at least one hydrophilic domain and from the at least one hydrophobic domain; and combining the compound and the carrier agent.

17. The method of claim 16 wherein the at least one hydrophobic domain comprises at least one lipid, at least one tocopherol, at least one hydrophobic oligomer or at least one hydrophobic polymer.

* * * * *